US007932036B1

(12) United States Patent
Raponi et al.

(10) Patent No.: US 7,932,036 B1
(45) Date of Patent: Apr. 26, 2011

(54) METHODS OF DETERMINING ACUTE MYELOID LEUKEMIA RESPONSE TO TREATMENT WITH FARNESYLTRANSFERASE

(75) Inventors: Mitch Raponi, San Diego, CA (US); Yixin Wang, Basking Ridge, NJ (US); Hongtao Fan, Audubon, PA (US)

(73) Assignee: Veridex, LLC, Raritan, NJ (US)

( * ) Notice: Subject to any disclaimer, the term of this patent is extended or adjusted under 35 U.S.C. 154(b) by 471 days.

(21) Appl. No.: 12/046,902

(22) Filed: Mar. 12, 2008

(51) Int. Cl.
*C12Q 1/68* (2006.01)
*C12P 19/34* (2006.01)
*C07H 21/02* (2006.01)

(52) U.S. Cl. ............. 435/6; 436/64; 436/63; 536/23.1
(58) Field of Classification Search .................. None
See application file for complete search history.

(56) References Cited

U.S. PATENT DOCUMENTS

| | | |
|---|---|---|
| 4,773,455 A | 9/1988 | Lessard |
| 5,238,922 A | 8/1993 | Graham et al. |
| 5,242,974 A | 9/1993 | Holmes |
| 5,384,261 A | 1/1995 | Winkler et al. |
| 5,405,783 A | 4/1995 | Pirrung et al. |
| 5,412,087 A | 5/1995 | McGall et al. |
| 5,420,245 A | 5/1995 | Brown et al. |
| 5,424,186 A | 6/1995 | Fodor et al. |
| 5,429,807 A | 7/1995 | Matson et al. |
| 5,436,327 A | 7/1995 | Southern et al. |
| 5,445,934 A | 8/1995 | Fodor et al. |
| 5,472,672 A | 12/1995 | Brennan |
| 5,491,164 A | 2/1996 | De Solms et al. |
| 5,504,212 A | 4/1996 | De Solms et al. |
| 5,523,430 A | 6/1996 | Patel et al. |
| 5,527,681 A | 6/1996 | Holmes |
| 5,529,756 A | 6/1996 | Brennan |
| 5,532,128 A | 7/1996 | Eggers |
| 5,532,359 A | 7/1996 | Marsters et al. |
| 5,534,537 A | 7/1996 | Ciccarone et al. |
| 5,545,531 A | 8/1996 | Rava et al. |
| 5,554,501 A | 9/1996 | Coassin et al. |
| 5,556,752 A | 9/1996 | Lockhart et al. |
| 5,561,072 A | 10/1996 | Saito |
| 5,571,639 A | 11/1996 | Hubbell et al. |
| 5,578,629 A | 11/1996 | Ciccarone et al. |
| 5,585,359 A | 12/1996 | Breslin et al. |
| 5,593,838 A | 1/1997 | Zanzucchi et al. |
| 5,599,695 A | 2/1997 | Pease et al. |
| 5,602,098 A | 2/1997 | Sebti et al. |
| 5,624,711 A | 4/1997 | Sundberg et al. |
| 5,658,734 A | 8/1997 | Brock et al. |
| 5,661,161 A | 8/1997 | Anthony et al. |
| 5,700,806 A | 12/1997 | Doll et al. |
| 5,721,236 A | 2/1998 | Bishop et al. |
| 5,750,567 A | 5/1998 | Baudoin et al. |
| 5,756,528 A | 5/1998 | Anthony |
| 5,767,274 A | 6/1998 | Kim |
| 5,780,492 A | 7/1998 | Dinsmore et al. |
| 5,807,852 A | 9/1998 | Doll et al. |
| 5,843,941 A | 12/1998 | Marsters et al. |
| 5,852,010 A | 12/1998 | Graham et al. |
| 5,856,326 A | 1/1999 | Anthony et al. |
| 5,856,439 A | 1/1999 | Clerc |
| 5,859,015 A | 1/1999 | Graham et al. |
| 5,861,529 A | 1/1999 | Baudoin et al. |
| 5,869,682 A | 2/1999 | DeSolms |
| 5,872,135 A | 2/1999 | DeSolms |
| 5,880,140 A | 3/1999 | Anthony |
| 5,889,053 A | 3/1999 | Baudoin et al. |
| 5,891,889 A | 4/1999 | Anthony et al. |
| 5,936,097 A | 8/1999 | Commerçon et al. |
| 5,939,557 A | 8/1999 | Anthony et al. |
| 5,958,939 A | 9/1999 | Afonso et al. |
| 5,965,539 A | 10/1999 | Sebti et al. |
| 5,965,578 A | 10/1999 | Graham et al. |
| 5,968,952 A | 10/1999 | Venet et al. |
| 5,968,965 A | 10/1999 | Dinsmore et al. |
| 5,972,966 A | 10/1999 | DeSolms |
| 5,972,984 A | 10/1999 | Anthony et al. |
| 5,976,851 A | 11/1999 | Brown et al. |
| 6,004,755 A | 12/1999 | Wang |
| 6,037,350 A | 3/2000 | Venet et al. |

(Continued)

OTHER PUBLICATIONS del Poeta et al. Blood 2003, 101:2125-2131.
* Hill, et al. "Inhibition of RAS-targeted prenylation: protein farnesyl transferase inhibitors revisited." Critical Reviews in Oncology/Hematology, Jan. 2003, vol. 33 No. 1 pp. 7-23.
Mosesso, et al. "The novel human gene aprataxin is directly involved in DNA single-strand-break repair." Cellular and Molecular Life Sciences, Feb. 2005, vol. 62, No. 4, pp. 485-491.
Zimmerman, et al., "Dose-Ranging Pharmacodynamic Study of Tipifarnib (R115777) in Patients With Relapsed and Refractory Hematologic Malignancies" American Society of Clinical Oncology, Dec. 2004, vol. 22, No. 23, pp. 4816-4822.
Nowicki, et al., "Chronic myelogenous leukemia molecular signature" Oncogene, Jun. 2003, vol. 22, No. 25, pp. 3952-3963.

(Continued)

*Primary Examiner* — Sarae Bausch
(74) *Attorney, Agent, or Firm* — Todd Volyn

(57) ABSTRACT

We analyzed bone marrow from 67 patients from a phase 2 study of farnesyltransferase inhibition with tipifarnib (R115777, ZARNESTRA®), in older adults with previously untreated, poor-risk acute myeloid leukemia (AML) for N-Ras mutations, global gene expression, and/or quantitative PCR (qPCR) of specific genes. Microarray profiling identified a two-gene expression ratio (RASGRP1:APTX) which provided the greatest accuracy for predicting response to tipifarnib. We demonstrated that this classifier could predict response to tipifarnib in an independent set of 54 samples from relapsed or refractory AML, with a NPV and PPV of 92% and 28%, respectively (odds ratio of 4.4). Therefore, in both newly diagnosed and relapsed or refractory AML, this classifier improves the overall response rate by approximately 50% while maintaining a high NPV, and significantly improves patient overall survival. The two-gene classifier was also validated by qPCR in thirty AML samples from the same clinical study demonstrating a negative predictive value (NPV) and positive predictive value (PPV) of 81% and 50%, respectively (odds ratio of 4.3). These data indicate that a simple two-gene expression assay may have utility in diagnosing a population of AML patients who are more likely to respond to tipifarnib.

2 Claims, 6 Drawing Sheets

U.S. PATENT DOCUMENTS

| | | | |
|---|---|---|---|
| 6,133,305 | A | 10/2000 | Tang et al. |
| 6,169,096 | B1 | 1/2001 | Venet et al. |
| 6,177,432 | B1 | 1/2001 | Angibaud et al. |
| 6,187,786 | B1 | 2/2001 | Venet et al. |
| 6,218,114 | B1 | 4/2001 | Peck et al. |
| 6,218,122 | B1 | 4/2001 | Friend et al. |
| 6,271,002 | B1 | 8/2001 | Linsley et al. |
| 6,271,210 | B1 | 8/2001 | Sivaraman et al. |
| 6,284,764 | B1 | 9/2001 | Kath et al. |
| 6,306,897 | B1 | 10/2001 | Uckun et al. |
| 2005/0003422 | A1 | 1/2005 | Raponi |
| 2007/0048782 | A1 | 3/2007 | Raponi |

OTHER PUBLICATIONS

PCT International Search Report, PCT application No. PCT/US08/56636, Alexandria, Virginia, dated Jul. 7, 2008, 5 pgs.

Ahel et al. (2006) The neurodegenerative disease protein aprataxin resolves abortive DNA ligation intermediates, Nature 443:713-716.

Bivona et al. (2003) Phospholipase Cgamma activates Ras on the Golgi apparatus by means of RasGRP1, Nature 424:694-698.

Bos (1989) Ras Oncogenes in Human Cancer: A review, Cancer Res 49:4682-4689.

Bullinger et al. (2004) Use of Gene-Expression Profiling to Identify Prognostic Subclasses in Adult Acute Myeloid Leukemia, N Engl J Med 350:1605-1616.

Burger et al. (2005) Activating Mutations in c-KIT and PDGFRalpha Are Exclusively Found in Gastrointestinal Stromal Tumors and Not in Other Tumors Overexpressing these Imatinib Mesylate Target Genes, Cancer Biol Ther 4:1270-1274.

Chang et al. (2003) Gene expression profiling for the prediction of therapeutic response to docetaxel in patients with breast cancer, Lancet 362:362-369.

Chen et al. (2005) FLT3/ITD Mutation Signaling Includes Suppression of SHP-1, J Biol Chem 280:5361-5369.

Cox et al (2002) Farnesyltransferase inhibitors: promises and realities, Curr Opin Pharmacol 2:388-393.

Ebinu et al. (1998) RasGRP, a Ras Guanyl Nucleotide- Releasing Protein with Calcium- and Diacylglycerol-Binding Motifs, Science 280:1082-1086.

Ehmann et al. (2006) Detection of N-RAS and K-RAS in their active GTP-bound form in acute myeloid leukemia without activating RAS mutations Leuk Lymphoma 47:1387-1391.

End et al. (2001) Characterization of the Antitumor Effects of the Selective Farnesyl Protein Transferase Inhibitor R115777 in Vivo and in Vitro, Cancer Res 61:131-137.

Feldkamp et al. (2001) Isotype-specific RasGTP-Levels Predict the Efficacy of Farnesyl Transferase Inhibitors against Human Astrocytomas regardless of Ras Mutational Status, Cancer Res 61:4425-4431.

Geman et al. (2004) Classifying Gene Expression Profiles from Pairwise mRNA Comparisons, Stat Appl Genet Mol Biol 3:30.

Holleman et al. (2004) Gene-Expression Patterns in Drug-Resistant Acute Lymphoblastic Leukemia Cells and Response to Treatment, N Engl J Med 351:533-542.

Illmer et al. (2005) Activation of the RAS Pathway Is Predictive for a Chemosensitive Phenotype of Acute Myelogenous Leukemia Blasts, Clin Cancer Res 11:3217-322.

Jansen et al. (2005) Molecular Classification of Tamoxifen-Resistant Breast Carcinomas by Gene Expression Profiling, J Clin Oncol 23:732-740.

Karp et al. (2001) Clinical and biologic activity of the farnesyltransferase inhibitor R115777 in adults with refractory and relapsed acute leukemias: a phase 1 clinical-laboratory correlative trial, Blood 97:3361-3369.

Kawasaki et al. (1998) A Rap guanine nucleotide exchange factor enriched highly in the basal ganglia, Proc Natl Acad Sci 95:13278-13283.

Lancet et al. (2006) A phase II study of the farnesyltransferase inhibitor tipifarnib in poor-risk and elderly patients with previously untreated acute myelogenous leukemia, Blood 2:2.

Lossos et al. (2004) Prediction of Survival in Diffuse Large-B-Cell Lymphoma Based on the Expression of Six Genes, N Engl J Med 350:1828-1837.

Lubet et al. (2006) Effects of the farnesyl transferase inhibitor R115777 (Zarnestra) on mammary carcinogenesis: prevention, therapy, and role of HaRas mutations, Mol Cancer Ther 5:1073-1078.

Lynch et al. (2004) Activating Mutations in the Epidermal Growth Factor Receptor Underlying Responsiveness of Non-Small-Cell Lung Cancer to Gefitinib, N Engl J Med 350:2129-2139.

Ma et al. (2004) A two-gene expression ratio predicts clinical outcome in breast cancer patients treated with tamoxifen, Cancer Cell 5:607-616.

Mesa (2006) Tipifarnib: farnesyl transferase inhibition at a crossroads, Expert Rev Anticancer Ther 6:313-319.

Moroni et al. (2005) Gene copy Number for epidermal growth factor receptor (EGFR) and clinical response to antiEGFR treatment in colorectal cancer: a cohort study, Lancet Oncol 6:279-286.

Perez De Castro et al. (2004) A Ras Activation in Jurkat T Cells following Low-Grade Stimulation of the T-Cell Receptor Is Specific to N-Ras and Occurs Only on the Golgi Apparatus, Mol Cell Biol 24:3485-3496.

Potti et al. (2006) Genomic signatures to guide the use of chemotherapeutics, Nat Med 12:1294-1300.

Rao et al. (2004) Phase III Double-Blind Placebo-Controlled Study of Farnesyl Transferase Inhibitor R115777 in Patients With Refractory Advanced Colorectal Cancer J Clin Oncol 22:3950-3957.

Reuter et al. (2000) Targeting the Ras signaling pathway: a rational, mechanism-based treatment for hematologic malignancies?, Blood 96:1655-1669.

Reuther et al. (2001) Leukemia-associated Rho Guanine Nucleotide Exchange factor, a Dbl Family Protein Found Mutated in Leukemia, Causes Transformation by Activation of RhoA, J Biol Chem 276:27145-27151.

Reuther et al. (2002) RasGRP4 is a Novel Ras Activator Isolated from Acute Myeloid Leukemia, J Biol Chem 277:30508-30514.

Rosenwald et al. (2002) The Use of Molecular Profiling to Predict Survival After Chemotherapy for Diffuse Large-B-Cell Lymphoma, N Engl J Med 346:1937-1947.

Rowinsky et al (1999) Ras Protein Farnesyltransferase: A Strategic Target for Anticancer Therapeutic Development, J Clin Oncol 17:3631-3652.

Sahai et al. (2002) RHO-GTPases and Cancer, Nat Rev Cancer 2:33-142.

Seidman et al. (2001) Weekly Trastuzumab and Paclitaxel Therapy for Metastatic Breast Cancer with Analysis of Efficacy by HER2 Immunophenotype and Gene Amplification, J Clin Oncol 19:2587-2595.

Ship et al. (2002) Diffuse large B-cell lymphoma outcome prediction by gene-expression profiling and supervised machine learning, Nat Med 8:68-74.

Solit et al. (2006) BRAF mutation predicts sensitivity to MEK inhibition, Nature 439:358-362.

Sterpetti et al. (1999) Activation of the Lbc Rho exchange factor proto-oncogene by truncation of an extended C terminus that regulates transformation and targeting Mol Cell Biol 19:1334-1345.

Stone (2006) Regulation of Ras in lymphocytes: get a GRP Biochem Soc Trans 34:858-861.

Tognon et al. (1998) Regulation of RasGRP via a Phorbol Ester-Responsive C1 Domain, Mol Cell Biol 18:6995-7008.

Tsao et al. (2005) Erlotinib in Lung Cancer—Molecular and Clinical Predictors of Outcome, N Engl J Med 353:133-144.

Van Cutsem et al. (2004) Phase III Trial of Gemcitabine Plus Tipifarnib Compared With Gemcitabine Plus Placebo in Advanced Pancreatic Cancer, J Clin Oncol 22:1430-1438.

Watters et al. (2006) Developing gene expression signatures of pathway deregulation in tumors, Mol Cancer Ther 5:2444-2449.

Weinstein et al. (2006) Mechanisms of disease: Oncogene addiction—a rationale for molecular targeting in cancer therapy Nat Clin Pract Oncol 3:448-457.

Whyte et al. (1997) K- and N-Ras are Geranylgeranylated in Cells Treated with Farnesyl Protein Transferase Inhibitors, J Biol Chem 272:14459-14464.

Yeoh et al. (2002) Classification, subtype discovery, and prediction of outcome in pediatric acute lymphoblastic leukemia by gene expression profiling, Cancer Cell 1:133-143.

Hill et al., "Inhibition of RAS-targeted prenylation: protein farnesyl transferase inhibitors revisted," Critical Reviews in Oncology/Hematology, vol. 33, No. 1, pp. 7-23, Jan. 2003.

Mesesso et al., "The novel human gene aprataxin is directly involved in DNA single-strand-break repair," Cellular and Molecular Life Sciences, vol. 62, No. 4, pp. 485-491, Feb. 2005.

Nowicki et al., "Chronic myelogenous leukemia molecular signature," Oncogene, vol. 22, No. 25, pp. 3952-3963, Jun. 2003.

Zimmerman et al., "Dose-Ranging Pharmacodynamic Study of Tipifarnib (R115777) in Patients with Relapsed and Refractory Hematologic Malignancies," American Society of Clinical Oncology, vol. 22, No. 23, pp. 4816-4822, Dec. 2004.

\* cited by examiner

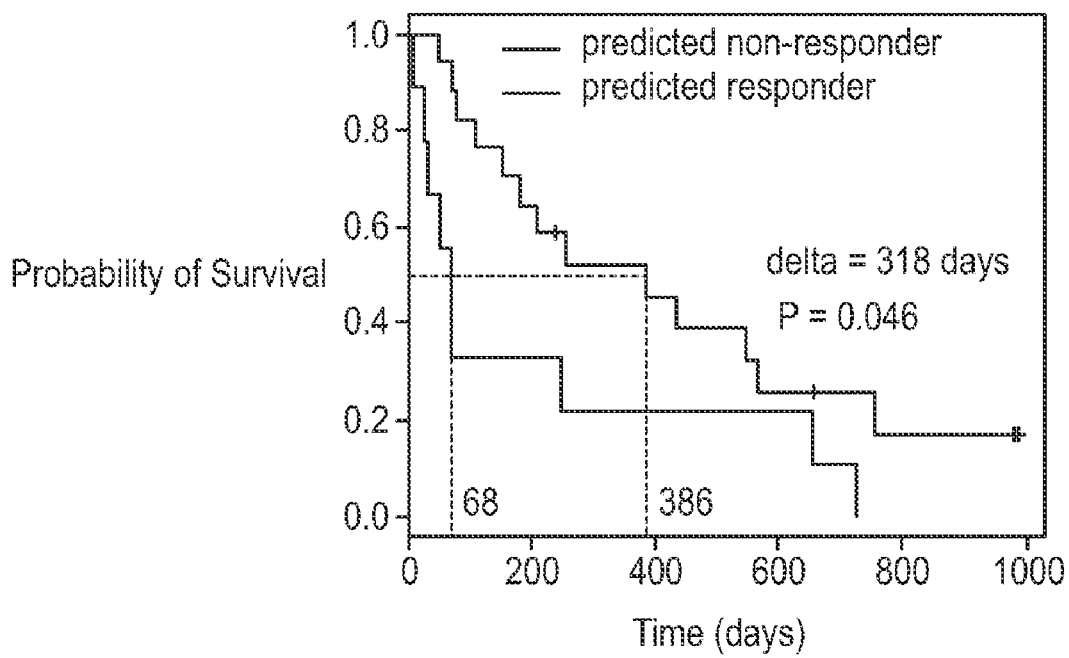

|       | PD | R  |    |
|-------|----|----|----|
| False | 12 | 2  | 14 |
| True  | 1  | 11 | 12 |
|       | 13 | 13 | 26 |

Sensitivity = 84.6%
Specificity = 92.3%
NPV = 85.7%
PPV = 91.7%
Prevalence = 50%

|  | PD | R |  |
|---|---|---|---|
| False | 23 | 2 | 25 |
| True | 21 | 8 | 29 |
|  | 44 | 10 | 54 |

Sensitivity = 80%
Specificity = 52.3%
NPV = 92%
PPV = 27.6%
Prevalence = 18.5%
Odds ratio = 4.38

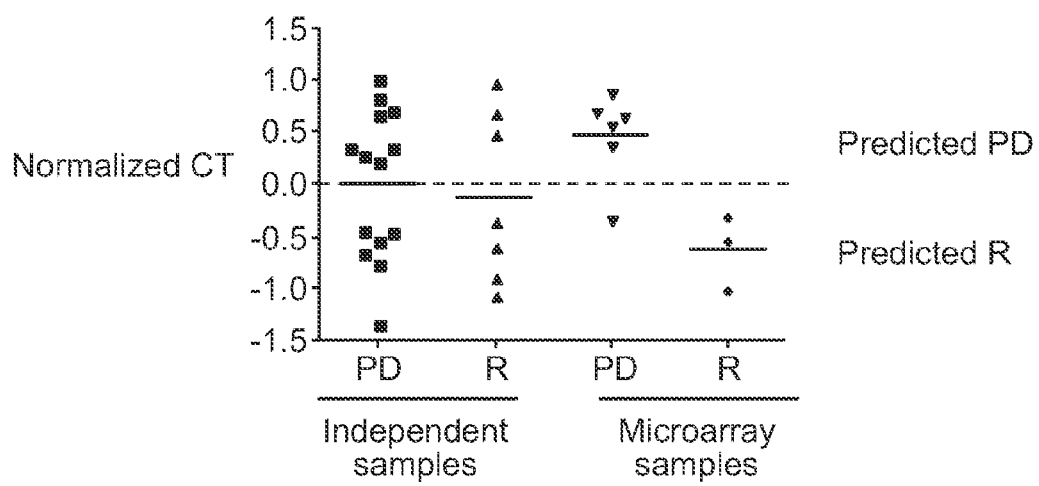
FIG. 3A
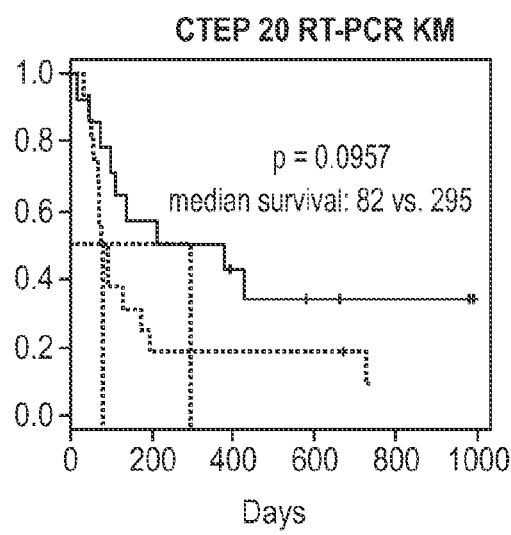
FIG. 3B
FIG. 3C

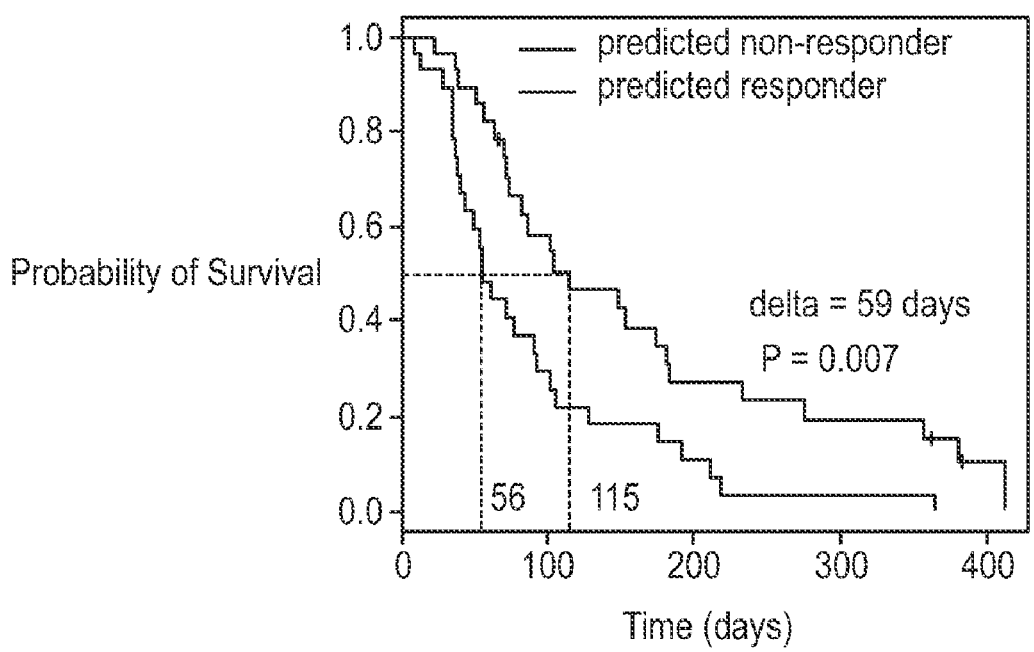

METHODS OF DETERMINING ACUTE MYELOID LEUKEMIA RESPONSE TO TREATMENT WITH FARNESYLTRANSFERASE

BACKGROUND OF THE INVENTION

Currently there is no method available to predict response to farnesyltransferase inhibitors. Tipifarnib was the first farnesyltransferase inhibitor (FTI) to be tested in the clinic. Rowinsky et al. (2006). It has demonstrated significant activity in hematological disorders including AML, MM, MDS and CML, with complete response rates in AML and MDS of up to approximately 15%. Mesa et al. (2006); Karp et al. (2001); Lancet et al. (2007); Fenaux et al. (2007); and Harousseau et al. (2007). FTIs function by competitively inhibiting the addition of a farnesyl moiety to a number of important signaling molecules including Ras. Rowinsky et al. (2006); and Cox et al. (2002).

Some molecules, such as Ras, that are implicated in cancers must be farnesylated by the farnesyl transferase enzyme in order to interact with the inner leaflet of the plasma membrane of the cell and become involved in various signaling pathways. Ras is not the only protein implicated in cancer that has a CAAX box that is prenylated. Farnesyl transferase inhibitors (FTIs) are therapeutic agents that inhibit the covalent attachment of the carbon farnesyl moieties to the C-terminal CAAX motif of various proteins. They have utility in the treatment of cancers and proliferative disorders such as leukemia. Acute myelogenous leukemia (AML) is among the diseases that can most beneficially be addressed with FTIs.

As is true in the case of many treatment regimens, some patients respond to treatment with FTIs and others do not. Prescribing the treatment to a patient who is unlikely to respond to it is not desirable. Thus, it would be useful to know how a patient could be expected to respond to such treatment before a drug is administered so that non-responders would not be unnecessarily treated and so that those with the best chance of benefiting from the drug are properly treated and monitored. Further, of those who respond to treatment, there may be varying degrees of response. Treatment with therapeutics other than FTIs or treatment with therapeutics in addition to FTIs may be beneficial for those patients who would not respond to FTIs or in whom response to FTIs alone is less than desired.

Historically, the mutation status of the ras gene was considered to be a candidate biomarker for patient response to FTIs. This rationale was based on pre-clinical evidence that FTIs could block Ras-transformed cells, and that specific point mutations within ras genes cause constitutive activation of the Ras pathway in many cancers. End et al. (2001) Reuter et al. (2000); and Bos et al. (1989). Since it is generally accepted that tumors are heavily reliant on the activation of one or two pathways ("oncogene addiction" hypothesis), it follows that patients whose tumors are promoted by a particular pathway should respond to drugs that inhibit that pathway. Weinstein et al. (2006). However, pathways can be activated by multiple events and it has been found that Ras can be up-regulated in the absence of activating Ras mutations. Ehmann et al. (2006). Furthermore, no correlation between ras mutations and response to FTIs has been demonstrated in clinical studies. Karp et al. (2001); and 20070048782. Indeed, while several early clinical studies focused on cancers that exhibited high frequencies of ras mutations the response rate was disappointingly low in those trials. Mesa (2006); Rao et al. (2004); and Van Cutwem et al. (2004).

SUMMARY OF THE INVENTION

We analyzed bone marrow from 67 patients from a phase 2 study of farnesyltransferase inhibition with tipifarnib (R115777, ZARNESTRA®), in older adults with previously untreated, poor-risk acute myeloid leukemia (AML) for N-Ras mutations, global gene expression, and/or quantitative PCR (qPCR) of specific genes. Microarray profiling identified a two-gene expression ratio (RASGRP1:APTX) which provided the greatest accuracy for predicting response to tipifarnib. We demonstrated that this classifier could predict response to tipifarnib in an independent set of 54 samples from relapsed or refractory AML, with a NPV and PPV of 92% and 28%, respectively (odds ratio of 4.4). Therefore, in both newly diagnosed and relapsed or refractory AML, this classifier improves the overall response rate by approximately 50% while maintaining a high NPV, and significantly improves patient overall survival. The two-gene classifier was also validated by qPCR in thirty AML samples from the same clinical study demonstrating a negative predictive value (NPV) and positive predictive value (PPV) of 81% and 50%, respectively (odds ratio of 4.3). These data indicate that a simple two-gene expression assay may have utility in diagnosing a population of AML patients who are more likely to respond to tipifarnib.

Microarray technology has been utilized to identify gene expression profiles that are predictive of response or resistance to a number of different therapeutic modalities in a variety of cancers, including chemotherapies or endocrine therapies in breast cancer, diffuse large b-cell lymphoma and leukemia. Ma et al. (2004); Chang et al. (2003) Jansen et al. (2005); Potti et al. (2006); Shipp et al. (2002); Rosenwald et al. (2002); Lossos et al. (2004); Yeoh et al. (2002) and Holleman et al. (2004). We have previously used gene expression profiling to identify molecular predictors of response to tipifarnib in relapsed or refractory AML. 20070048782. Here we have extended this work to newly diagnosed AML which has led to the identification of a two-gene expression ratio (RASGRP1:APTX) that is predictive of clinical outcome. We further show that this classifier can be assayed by qPCR and that it also has predictive utility in relapsed or refractory AML.

BRIEF DESCRIPTION OF THE DRAWINGS

FIG. 1 depicts the performance of the RASGRP1 gene as a predictor of response to tipifarnib in AML. The accuracy rates (A) and Kaplan-Meier survival curves (B) using the RASGRP1 gene classifier in newly diagnosed AML.

FIG. 3 depicts the performance of RASGRP1:APTX gene classifier using qPCR. (A) The normalized RASGRP1:APTX Ct values for 20 responders and 10 patients with progressive disease. The 20 independent samples and 10 training samples that were run on microarray are shown separately. Horizontal bars indicate group means. (B) The accuracy rates of the RASGRP1 gene classifier in newly diagnosed AML for all 30 patients are shown using a cutoff of 0 was used to stratify patients. (C) The associated overall survival of the stratified patients are plotted using Kaplan-Meier analysis.

FIG. 4 depicts the performance of the RASGRP1 gene as a predictor of response to tipifarnib in relapsed and refractory AML. The accuracy rates (A) and Kaplan Meier survival curves (B) using the RASGRP1 gene classifier in relapsed/refractory AML.

DETAILED DESCRIPTION OF THE INVENTION

Figures 2A, 2B:
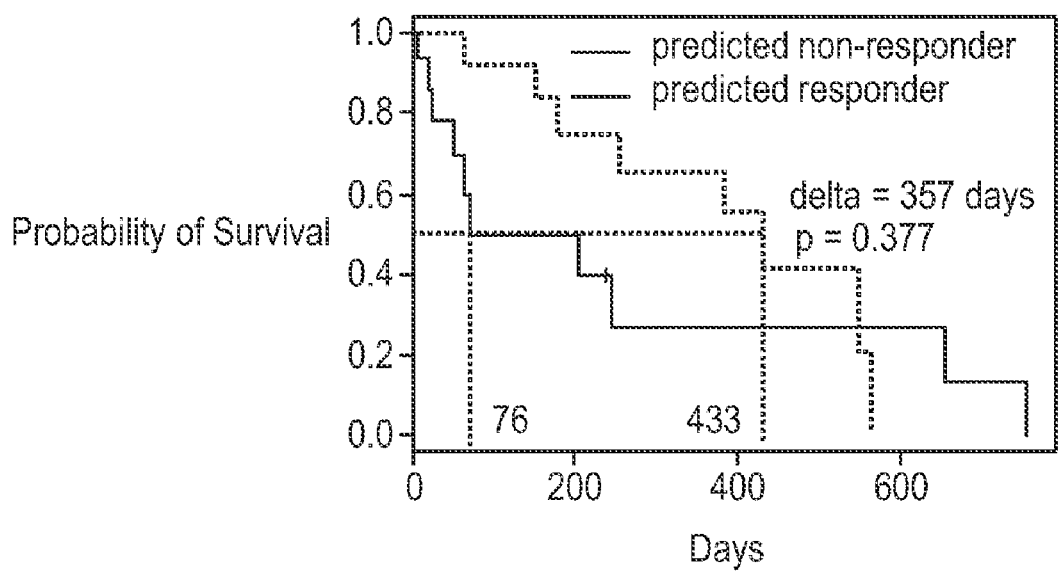
FIG. 2 depicts the performance of the RASGRP1:APTX gene pair as a predictor of response to tipifarnib in AML. The overall survival of newly diagnosed AML patients (A) and relapsed/refractory AML patients (C) stratified with the 2-gene classifier are plotted using Kaplan-Meier analysis. The accuracy rates of the two-gene classifier in newly diagnosed AML (B) and relapsed/refractory AML (D) are shown.

The therapeutic agents referred to in this specification are FTIs. They take on a multitude of forms but share the essential inhibitory function of interfering with or lessening the farnesylation of proteins implicated in cancer and proliferative diseases. Preferably, the FTIs are those indicated for the treatment of leukemias such as AML. A patient who responds to an FTI is one in whom a reduction of more than 50% of blast cells is seen in bone marrow following treatment with the FTI.

Numerous FTIs are within the scope of the invention and include those described in U.S. Pat. Nos. 5,976,851; 5,972,984; 5,972,966; 5,968,965; 5,968,952; 6,187,786; 6,169,096; 6,037,350; 6,177,432; 5,965,578; 5,965,539; 5,958,939; 5,939,557; 5,936,097; 5,891,889; 5,889,053; 5,880,140; 5,872,135; 5,869,682; 5,861,529; 5,859,015; 5,856,439; 5,856,326; 5,852,010; 5,843,941; 5,807,852; 5,780,492; 5,773,455; 5,767,274; 5,756,528; 5,750,567; 5,721,236; 5,700,806; 5,661,161; 5,602,098; 5,585,359; 5,578,629; 5,534,537; 5,532,359; 5,523,430; 5,504,212; 5,491,164; 5,420,245; and 5,238,922. Non-peptidal, so-called "small molecule" therapeutics are preferred. More preferred FTIs are quinolines or quinoline derivatives such as:
7-(3-chlorophenyl)-9-[(4-chlorophenyl)-1H-imidazol-1-yl-methyl]-2,3-dihydro-o-1H,5H-benzo[ij]quinolizin-5-one,
7-(3-chlorophenyl)-9-[(4-chlorophenyl)-1H-imidazol-1-yl-methyl]-1,2-dihydro-o-4H-pyrrolo[3,2,1-ij]quinoline-4-one,
8-[amino(4-chlorophenyl)(1-methyl-1H-imidazol-5-yl),methyl]-6-(3-chloroph-enyl)-1,2-dihydro-4H-pyrrolo[3,2,1-ij]quinolin-4-one, and
8-[amino(4-chlorophenyl)(1-methyl-1H-imidazol-5-yl)methyl]-6-(3-chlorophe-nyl)-2,3-dihydro-1H,5H-benzo[ij]quinolizin-5-one. The most preferred FTI is (B)-6-[amino (4-chlorophenyl)(1-methyl-1H-imidazol-5-yl)methyl]-4-(3-ch-lorophenyl)-1-methyl-2(1H)-quinolinone).

In the aspect of the invention comprising treating leukemia with FTIs and other therapeutic agents, the therapeutic agents referred to in this specification are those that have an effect on the biological pathway explicated through the gene expression analysis of leukemic cells subjected to treatment with quinilone-based FTIs.

The mere presence of nucleic acid sequences having the potential to express proteins or peptides ("genes") within the genome is not determinative of whether a protein or peptide is expressed in a given cell. Whether or not a given gene capable of expressing proteins or peptides does so and to what extent such expression occurs, if at all, is determined by a variety of complex factors. Irrespective of difficulties in understanding and assessing these factors, assaying gene expression can provide useful information about the cellular response to a given stimulus such as the introduction of a drug or other therapeutic agent. Relative indications of the degree to which genes are active or inactive can be found in gene expression profiles. The gene expression profiles of this invention are used to identify and treat patients who will likely benefit from a given therapy or exclude patients from a given therapy where the patient likely would experience little or no beneficial response to the drug or therapy.

Preferred methods for establishing gene expression profiles (including those used to arrive at the explication of the relevant biological pathways) include determining the amount of RNA that is produced by a gene that can code for a protein or peptide. This is accomplished by reverse transcription PCR (RT-PCR), competitive RT-PCR, real time RT-PCR, differential display RT-PCR, Northern Blot analysis and other related tests. While it is possible to conduct these techniques using individual PCR reactions, it is best to amplify copy DNA (cDNA) or copy RNA (cRNA) produced from mRNA and analyze it via microarray. A number of different array configurations and methods for their production are known to those of skill in the art and are described in U.S. Patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637.

Microarray technology allows for the measurement of the steady-state mRNA level of thousands of genes simultaneously thereby presenting a powerful tool for identifying the effect of FTIs on cell biology and the likely effect of treatment based on analysis of such effects. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA, expressed in the sample cells. A large number of such techniques are available and useful. Preferred methods for determining gene expression can be found in U.S. Pat. Nos. 6,271,002; 6,218,122; 6,218,114; and 6,004,755.

Analysis of the expression levels is conducted by comparing such intensities. This is best done by generating a ratio matrix of the expression intensities of genes in a test sample versus those in a control sample. For instance, the gene expression intensities from a tissue that has been treated with a drug can be compared with the expression intensities generated from the same tissue that has not been treated with the drug. A ratio of these expression intensities indicates the fold-change in gene expression between the test and control samples.

Gene expression profiles can also be displayed in a number of ways. The most common method is to arrange a ratio matrix into a graphical dendogram where columns indicate test samples and rows indicate genes. The data is arranged so genes that have similar expression profiles are proximal to each other. The expression ratio for each gene is visualized as a color. For example, a ratio less than one (indicating down-regulation) may appear in the blue portion of the spectrum while a ratio greater than one (indicating up-regulation) may appear as a color in the red portion of the spectrum. Commercially available computer software programs are available to display such data including "OMNIVIZ PRO" software from Batelle and "TREE VIEW" software from Stanford The genes that are differentially expressed are either up regulated or down regulated in diseased cells following treatment with an FTI. Up regulation and down regulation are relative terms meaning that a detectable difference (beyond the contribution of noise in the system used to measure it) is found in the amount of expression of the genes relative to some baseline. In this case, the baseline is the measured gene expression of the untreated diseased cell. The genes of interest in the treated diseased cells are then either up regulated or down regulated relative to the baseline level using the same measurement method. Preferably, levels of up and down regulation are distinguished based on fold changes of the intensity measurements of hybridized microarray probes. A 1.5 fold difference is preferred for making such distinctions. That is, before a gene is said to be differentially expressed in treated versus untreated diseased cells, the treated cell is found to yield at least 1.5 times more, or 1.5 times less intensity than the untreated cells. A 1.7 fold difference is more preferred and a 2 or more fold difference in gene expression measurement is most preferred.

A portfolio of genes is a set of genes grouped so that information obtained about them provides the basis for making a clinically relevant judgment such as a diagnosis, prognosis, or treatment choice. In this case, the judgments supported by the portfolios involve the treatment of leukemias with FTI's. Portfolios of gene expression profiles can be comprised of combinations of genes.

One method of the invention involves comparing gene expression profiles for various genes to determine whether a person is likely to respond to the use of a therapeutic agent. Having established the gene expression profiles that distinguish responder from non-responder, the gene expression profiles of each are fixed in a medium such as a computer readable medium as described below. A patient sample is obtained that contains diseased cells (such as hematopoietic blast cells in the case of AML) is then obtained. Sample RNA is then obtained and amplified from the diseased patient cell and a gene expression profile is obtained, preferably via micro-array, for genes in the appropriate portfolios. The expression profiles of the samples are then compared to those previously determined as responder and non-responder. If the sample expression patterns are consistent with an FTI responder expression pattern then treatment with an FTI could be indicated (in the absence of countervailing medical considerations). If the sample expression patterns are consistent with an FTI non-responder expression pattern then treatment with an FTI would not be indicated. Preferably, consistency of expression patterns is determined based on intensity measurements of micro-array reading as described above.

In similar fashion, gene expression profile analysis can be conducted to monitor treatment response. In one aspect of this method, gene expression analysis as described above is conducted on a patient treated with an FTI at various periods throughout the course of treatment. If the gene expression patterns are consistent with a responder then the patient's therapy is continued. If it is not, then the patient's therapy is altered as with additional therapeutics such as tyrosine kinase inhibitor, changes to the dosage, or elimination of FTI treatment. Such analysis permits intervention and therapy adjustment prior to detectable clinical indicia or in the face of otherwise ambiguous clinical indicia.

It is possible to attain ambiguous results in which some gene expression profiles are recorded that are in some respects indicative of a responder and in other respects indicative of a non-responder. For example, the profiles may show that three genes are up-regulated consistent with a responder but that another gene is not up-regulated as would ordinarily be the case for a responder. In such a case, statistical algorithms can be applied to determine the probability that the patient will respond or not respond to the drug. Statistical algorithms suitable for this purpose are well known and are available.

Articles of this invention are representations of the gene expression profiles useful for treating, diagnosing, prognosticating, staging, and otherwise assessing diseases that are reduced to a medium that can be automatically read such as computer readable media (magnetic, optical, and the like). The articles can also include instructions for assessing the gene expression profiles in such media. For example, the articles may comprise a CD ROM having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. FIG. 1 shows an example of the graphical display of such a recordation. Clustering algorithms such as those incorporated in "OMNIVIZ" and "TREE VIEW" computer programs mentioned above can best assist in the visualization of such data.

Additional articles according to the invention are nucleic acid arrays (e.g. cDNA or oligonucleotide arrays), as described above, configured to discern the gene expression profiles of the invention.

Using clustering analysis (including the algorithms mentioned above) one can compare the expression levels of patient samples to establish regulatory relationships among genes with a certain statistical confidence. A dynamic map was constructed based upon such expression data. Such a genetic network map is useful for drug discovery. For example, once basic genes of interest were identified, a list of potential up-stream regulatory genes was found using such a genetic network map. The genes so identified or their expression products were then analyzed for their use as drug targets. In some embodiments, the regulatory function of the particular genes identified was used to identify therapeutics for use in treating leukemia.

The regulation of transcription, RNA processing and RNA editing are all accomplished by proteins which are coded by their own genes. In addition, DNA sequences can exert long-range control over the expression of other genes by positional effects. Therefore, the expression of genes is often regulated by the expression of other genes. Those regulatory genes are called upstream genes, relative to the regulated or downstream genes. In a simple regulatory pathway: A++>B--> C++>D where: A, B, C, D are genes ++ up-regulates -- down-regulates Gene A is an up-stream gene of gene B and B is an up-stream gene of C. One of skill in the art would appreciate that the network is frequently looped and interconnected. In some instances, the expression of a gene is regulated by its own product as either a positive or negative feedback.

Cluster analysis methods were used to group genes whose expression level is correlated. Methods for cluster analysis are described in detail in Harfigan (1975) Clustering Algorithms, NY, John Wile and Sons, Inc, and Everritt, (1980) Cluster Analysis 2nd. Ed. London Heineman Educational books, Ltd. Path analysis was used to decompose relations among variables and for testing causal models for the genetic networks. Multiple primary targets of a drug in leukemic cells were identified as were drugs/drug classes useful in treating such cells. According to the current invention, drugs are any compounds of any degree of complexity that perturb a biological system.

The biological effect of a drug may be a consequence of drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In addition to the FTI's that are preferred, the preferred drugs of this invention are those that modulate the MAPK/ERK signaling pathways, TGF-β, WNT or apoptotic pathways. These include, without limitation, tyrosine kinase inhibitors, MEK kinase inhibitors, P13K kinase inhibitors, MAP kinase inhibitors, apoptosis modulators and combinations thereof. Exemplary drugs that are most preferred among these are the "GLEEVEC" tyrosine kinase inhibitor of Novartis, U-0126 MAP kinase inhibitor, PD-098059 MAP kinase inhibitor, SB-203580 MAP kinase inhibitor, and antisense, ribozyme, and DNAzyme Bcl-XL anti-apoptotics. Examples of other useful drugs include, without limitation, the calanolides of U.S. Pat. No. 6,306,897; the substituted bicyclics of U.S. Pat. No. 6,284,764; the indolines of U.S. Pat. No. 6,133,305; and the antisense oligonucleotides of U.S. Pat. No. 6,271,210.

As noted, the drugs of the instant invention can be therapeutics directed to gene therapy or antisense therapy. Oligonucleotides with sequences complementary to an mRNA sequence can be introduced into cells to block the translation of the mRNA, thus blocking the function of the gene encoding the mRNA. The use of oligonucleotides to block gene expression is described, for example, in, Strachan and Read, Human Molecular Genetics, 1996.

These antisense molecules may be DNA, stable derivatives of DNA such as phosphorothioates or methylphosphonates, RNA, stable derivatives of RNA such as 2'-O-alkylRNA, or other antisense oligonucleotide mimetics. Antisense molecules may be introduced into cells by microinjection, liposome encapsulation or by expression from vectors harboring the antisense sequence.

In the case of gene therapy, the gene of interest can be ligated into viral vectors that mediate transfer of the therapeutic DNA by infection of recipient host cells. Suitable viral vectors include retrovirus, adenovirus, adeno-associated virus, herpes virus, vaccinia virus, polio virus and the like. Alternatively, therapeutic DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo gene therapy. Protocols for molecular methodology of gene therapy suitable for use with the gene is described in Gene Therapy Protocols, edited by Paul D. Robbins, Human press, Totowa N.J., 1996.

Pharmaceutically useful compositions comprising the drugs of this invention may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the drug. The effective amount of the drug may vary according to a variety of factors such as the individual's condition, weight, sex and age. Other factors include the mode of administration. The pharmaceutical compositions may be provided to the individual by a variety of routes such as subcutaneous, topical, oral and intramuscular.

The drugs of this invention include chemical derivatives of the base molecules of the drug. That is, they may contain additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition or activity while minimizing any potential toxicity. In addition, co-administration or sequential administration of other agents may be desirable.

The drugs of this invention can be administered in a wide variety of therapeutic dosage forms in conventional vehicles for administration. For example, the drugs can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators used in the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators in the present invention is selected in accordance with a variety of factors including type, species, age, weight, sex and medical condition of the patient; the severity of the condition to be treated; the route of administration; the renal and hepatic function of the patient; and the particular drug employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The drugs of this invention can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

The drugs in the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Drugs in the present invention may also be delivered by the use of monoclonal antibodies as individual carriers to which the compound molecules are coupled. The drugs in the present invention may also be coupled with soluble polymers as targetable drug carriers. Such polymers can include polyvinyl-pyrrolidone, pyran copolymer, polyhydroxypropyl-methacryl-amidephenol, polyhydroxy-ethylaspartamidephenol, or polyethyl-eneoxidepolylysine substituted with palmitoyl residues. Furthermore, the drugs in the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the drugs may be administered in capsule, tablet, or bolus form or alternatively they can be mixed with feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the drugs and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered by simply mixing the compound with the feedstuff or by applying the compound to the surface of the foodstuff.

The compounds or modulators may alternatively be administered parenterally via injection of a formulation consisting of the active ingredient dissolved in an inert liquid carrier. Injection may be either intramuscular, intraluminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

All references cited herein are hereby incorporated herein by reference. The invention is further illustrated by the following non-limiting examples.

EXAMPLE 1

Materials and Methods

Clinical Evaluation

The current study utilized 67 bone marrow samples collected from an open label, multicenter, non-comparative phase 2 study investigating the efficacy and safety of farnesyltransferase inhibition with tipifarnib (R115777, ZARNESTRA®) in 158 older adults with previously untreated, poor-risk AML. The clinical results have been published elsewhere. Lancet et al. (2006).

Sample Collection and Processing

Bone marrow samples were collected from consenting patients before treatment with tipifarnib and mononuclear cells were processed on site. Bone marrow aspirates were diluted with PBS and centrifuged with ficoll-diatrizoate (1.077 g/ml). Enriched leukemic blood cells were washed twice with PBS, resuspended in FBS with 10% DMSO and immediately frozen at −70° C. to −80° C. Total RNA was extracted from cell samples using the Trizol Kit (Qiagen, Santa Clarita, Calif.). RNA quality was determined by assessing the presence of ribosomal bands on an Agilent Bioanalyzer. Good quality samples were further processed for microarray analysis. DNA was isolated from the same sample of Trizol-processed bone marrow as per the manufacturers instructions (Qiagen, Santa Clarita, Calif.). Samples were assayed for global gene expression, N-Ras mutations, and/or qPCR of specific genes (FIG. 1).

N-Ras Mutational Status

Analysis of activating mutations in N-ras was determined by PCR and RFLP analysis as previously described. End et al. (2001). Exons 1 and 2 of the N-ras gene were simultaneously amplified in a single multiplex reaction and an aliquot was used for a second round of PCR. Resistance to cleavage at natural or primer induced restriction enzyme sites in second-round amplicons indicated the presence of a mutation that had abolished the site at the loci being analyzed. Restriction enzymes for the analysis of specific loci were Bsl I (N-ras codons 12 and 13), Msc I (N-ras codon 61, positions 1 and 2), and Bfa I (N-ras codon 61, position 3). Reactions were digested overnight and PCR products were analyzed on an Agilent Bioanalyzer.

Microarray Analysis

Synthesis of cDNA and cRNA were performed according to Affymetrix (Santa Clara, Calif.) protocols. Since the yield of many samples was low two rounds of linear amplification was performed as previously described. 20070048782. For hybridization, 11 μg of cRNA were fragmented randomly by incubation at 94° C. for 35 min in 40 mM Tris-acetate, pH 8.1, 100 mM potassium acetate, and 30 mM magnesium acetate. Fragmented cRNA was hybridized to U133A arrays at 45° C. for 16 h in a rotisserie oven set at 60 rpm. Following hybridization, arrays were washed (with 6×SSPE and 0.5×SSPE containing Triton X-100 (0.005%)), and stained with streptavidin-phycoerythrin (SAPE; Molecular Probes, Eugene, Oreg.). Quantification of bound labeled probe was conducted using the Agilent G2500A GeneArray scanner (Agilent Technologies, Palo Alto, Calif.).

The total fluorescence intensity for each array was scaled to the uniform value of 600. Chip performance was quantified by calculating a signal to noise ratio (raw average signal/noise). Chips were removed from further analysis if their signal-to-noise ratio was less than 20 or if the present calls on the chip was less than 30%. Genes were only included in further analysis if they were called "present" in at least 10% of the chips. Approximately 12,000 Affymetrix probe sets remained following this cut-off. The quality of the gene expression data were further controlled by identifying outliers based on principal components analysis and by analyzing the normal distributions of the gene intensities (Partek Pro V5.1). The microarray data have been deposited in NCBIs Gene Expression Omnibus (GEO, http://www.ncbi.nlm.nih.gov/geo/) and are accessible through GEO Series accession number GSEXXXX.

Response Definitions

Response to tipifarnib is reported in the clinical paper and was defined as patients who had a complete response (CR), a partial response (PR), or hematological improvement (HI). Lancet et al. (2006). Briefly, HI was defined as any bone marrow blast count less than 5% or a reduction in bone marrow blasts by at least half. Progressive disease (PD) was defined as either >50% increase in bone marrow or circulating blast % from baseline, or new appearance of circulating blasts (on at least 2 consecutive occasions). Stable disease (SD) was defined as any response not meeting CR, PR, HI, or PD criteria.

Statistical Analysis

Receiver Operator Characteristic (ROC) analysis was utilized to test the overall predictive value of individual genes and/or multigene classifiers. The following gene filtering criteria were used to identify genes differentially expressed between responders and patients with progressive disease: Specificity for identifying "responder" with 100% sensitivity>=40%, T-test p value (log 2 transformed data with unequal variance)<0.05, fold change>2. The genes that passed these criteria were ranked by AUC (Area under the ROC curve).

To build a classifier the response score was used to calculate each patient's chance to response to tipifarnib therapy. The score was defined as the linear combination of weighted expression signals with the t statistic as the weight. The threshold was determined from the ROC curve of the training set to ensure 100% sensitivity and the highest specificity. To determine how many genes needed to be included in the predictor, leave-one-out cross validation (LOOCV) was carried out. The response scores for the 'left-out' samples based on different numbers of genes were recorded. The performances of the predictors with different numbers of genes were assessed based on misclassification error rate, sensitivity, specificity, p values measuring the separation of Kaplan-Meier curves of the two predicted groups. And the best predictor was selected accordingly.

The Top Scoring Pair (TSP) algorithm was first introduced by Geman et al. (2004). In essence, the algorithm ranks all the gene pairs (genes i and j) based on the absolute difference (Dij) in the frequency of event where gene i has higher expression value than gene j in samples among class C1 to C2. In the cases of there are multiple top scoring pairs (all sharing the same Dij), we select the top pair by a secondary rank score that measures the magnitude to which inversions of gene expression levels occur from one class to the other within a pair of genes. The top pair with highest frequency of absolute Dij>2 fold in all samples will be selected as candidate pair. The candidate pair was then assessed in an independent testing data set.

Leave-one-out cross validation (LOOCV) was carried out in the training data set to evaluate how the algorithm perform. The performances of the predictors were assessed based on maximum misclassification error rate. All the statistical analyses were done using R(R Development Core Team, 2006).

Real-Time Quantitative RT-PCR

For each sample, 1 μg of total RNA (as assessed by $OD_{260}$) was reversed transcribed using the High Capacity cDNA Reverse Transcription kit (Applied Biosystems, Foster City, Calif.) according to the manufacturers instructions. Samples were then incubated at 25° C. for 10 minutes and then 37° C. for 30 minutes for optimum RNA conversion. QPCR was performed using the ABI Prism 7900HT sequence detection system (Applied Biosystems, Foster City, Calif.) with all samples run in triplicate. Each reaction contained 5 μl Taq-Man® Universal PCR Master Mix containing UNG (Applied Biosystems, Foster City, Calif.), 4.5 μl of cDNA template and 0.5 μl of 20× Assay on Demand Gene Expression Assay Mix or 9 pmol of both forward and reverse primer and 2.5 pmol of probe (Applied Biosystems, Foster City, Calif.), in a total reaction volume of 10 μl. All primer, probe sets were chosen due to the small amplicon size (less than 100 nucleotides) and FAM fluorogenic probes were used. Primers and probes used were APTX (product number 4331182 Applied Biosystems) and RASGRP1 (product number 4351372 Applied Biosystems). The RASGRP1:APTX expression ratio was calculated by normalizing the raw Ct values by subtracting the mean Ct from the sample set, dividing by the standard deviation, and then calculating the difference of the normalized Ct values of each gene (APTX−RASGRP1). Ma et al. (2004).

Results

This study examined gene expression profiles of leukemic bone marrow samples from patients enrolled in a Phase 2 clinical trial of the farnesyltransferase inhibitor tipifarnib in elderly patients with previously untreated poor-risk acute myelogenous leukemia. Lancet et al. (2006). Bone marrow from 67 patients was collected before treatment with tipifarnib and leukemic myeloid cells were enriched by Ficoll-density centrifugation (Table 1). Good quality total RNA from 13 responders (9 CR, 4 HI), 8 stable disease and 13 progressive disease patients was amplified, labeled, and hybridized to the Affymetrix U133A GeneChip. A total of 30 samples were evaluated by qPCR for validation of specific genes and 32 samples were evaluated for N-Ras mutational status.

TABLE 1

Comparison of profiled patients.

| Parameter | All treated patients | PGx profiled patients |
|---|---|---|
| Total patients, n | 158 | 67 |
| microarray assay, n | | 34 |
| qPCR assay, n | | 30 |
| N-Ras assay, n | | 32 |
| N-Ras mutation, n (%) | | 11 (34) |
| median age, y (range) | 74 (34-85) | 73 (63-85) |

TABLE 1-continued

Comparison of profiled patients.

| Parameter | All treated patients | PGx profiled patients |
|---|---|---|
| sex, n male (%) | 95 (60) | 41 (61) |
| Prior MDS, yes (%) | 119 (75) | 48 (72) |
| CR, no. (%) | 22 (14) | 14 (21) |
| PR, no. (%) | 3 (2) | 1 (2) |
| HI, no. (%) | 12 (8) | 7 (10) |
| SD, no. (%) | 50 (32) | 15 (22) |
| PD, no. (%) | 58 (37) | 30 (44) |
| NE, no. (%) | 13 (8) | 0 (0) |

CR = complete response; PR = partial response; HI = hematological improvement, SD = stable disease, PD = progressive disease, NE = not evaluable; PGx = pharmacogenomics Ras mutational status and patient outcome DNA from the bone marrow of 32 AML patients was screened for N-Ras activating mutations (codons 12, 13, 61). Thirty-four percent (11/32) of patients exhibited N-Ras mutations with one patient having mutations at multiple codons (Table 2). There was no statistically significant correlation between N-Ras mutational status and response to tipifarnib or overall survival.

TABLE 2

| SUBJID | RESPONSE | N-Ras Mutation | OS | Alive | Microarray | qPCR | SEX | AGE | Prior MDS |
|---|---|---|---|---|---|---|---|---|---|
| 100101 | HI | ND | 378 | NO | ND | YES | MALE | 68 | NO |
| 100104 | PD | ND | 728 | NO | YES | YES | FEMALE | 63 | NO |
| 100109 | PD | ND | 68 | NO | YES | YES | FEMALE | 81 | NO |
| 100110 | CR | ND | 983 | YES | YES | YES | FEMALE | 74 | NO |
| 100112 | PD | ND | 169 | NO | ND | YES | FEMALE | 69 | YES |
| 100113 | CR | ND | 211 | NO | ND | YES | MALE | 82 | YES |
| 100116 | PD | ND | 14 | NO | ND | YES | FEMALE | 72 | YES |
| 100121 | SD | ND | 252 | NO | YES | ND | MALE | 72 | YES |
| 100204 | SD | N-12 | 493 | NO | ND | ND | FEMALE | 69 | YES |
| 100205 | PD | WT | 754 | NO | YES | ND | MALE | 74 | YES |
| 100208 | PD | WT | 29 | NO | YES | ND | MALE | 76 | YES |
| 100209 | PD | N61 (1, 2) | 209 | NO | YES | ND | MALE | 73 | YES |
| 100210 | PD | N-12, N-13 | 654 | NO | YES | ND | MALE | 68 | YES |
| 100212 | SD | N-12 | 1200 | YES | ND | ND | MALE | 70 | YES |
| 100213 | CR | WT | 257 | NO | YES | ND | FEMALE | 81 | YES |
| 100214 | CR | N-13 | 395 | NO | ND | ND | FEMALE | 73 | YES |
| 100215 | SD | WT | 54 | NO | ND | ND | MALE | 82 | NO |
| 100216 | SD | N-13 | 116 | NO | ND | ND | MALE | 77 | YES |
| 100302 | PD | N-12 | 48 | NO | YES | ND | FEMALE | 73 | NO |
| 100307 | HI | WT | 179 | NO | YES | ND | MALE | 68 | YES |
| 100310 | SD | WT | 242 | NO | ND | ND | FEMALE | 76 | YES |
| 100316 | SD | WT | 273 | NO | ND | ND | FEMALE | 66 | NO |
| 100317 | PD | WT | 39 | NO | ND | ND | MALE | 76 | NO |
| 100319 | SD | WT | 233 | NO | YES | ND | MALE | 71 | NO |
| 100320 | HI | WT | 374 | NO | ND | ND | FEMALE | 78 | NO |
| 100322 | CR | WT | 237 | YES | YES | ND | MALE | 73 | YES |
| 100324 | HI | WT | 248 | NO | YES | ND | MALE | 85 | YES |
| 100330 | HI | N-12 | 153 | NO | YES | ND | FEMALE | 67 | NO |
| 100333 | SD | N-12 | 364 | NO | YES | ND | MALE | 65 | YES |
| 100336 | CR | N-12 | 67 | NO | YES | ND | MALE | 80 | YES |
| 100337 | PD | WT | 38 | NO | ND | ND | MALE | 72 | YES |
| 100338 | PD | N-12 | 8 | NO | YES | ND | MALE | 78 | NO |
| 100339 | PD | WT | 25 | NO | YES | ND | MALE | 75 | NO |
| 100340 | SD | WT | 32 | NO | ND | ND | FEMALE | 83 | NO |
| 100341 | CR | WT | 433 | NO | YES | ND | MALE | 67 | YES |
| 100604 | SD | WT | 64 | NO | YES | ND | MALE | 63 | YES |
| 100605 | PD | WT | 74 | NO | ND | ND | MALE | 67 | YES |
| 101008 | CR | WT | 548 | NO | YES | ND | MALE | 82 | NO |
| 101021 | CR | ND | 991 | YES | YES | YES | FEMALE | 69 | YES |
| 101025 | CR | ND | 735 | YES | ND | YES | MALE | 70 | YES |
| 101029 | PD | ND | 64 | NO | ND | YES | MALE | 70 | YES |
| 101038 | SD | ND | 151 | NO | YES | ND | FEMALE | 75 | YES |
| 101039 | PD | ND | 50 | NO | ND | YES | FEMALE | 85 | YES |
| 101043 | SD | ND | 200 | NO | YES | ND | FEMALE | 79 | YES |
| 101046 | PD | ND | 53 | NO | YES | YES | FEMALE | 66 | YES |
| 101049 | CR | WT | 564 | NO | YES | ND | MALE | 65 | YES |
| 101057 | CR | WT | 386 | NO | YES | ND | MALE | 85 | YES |
| 101067 | PD | ND | 88 | NO | ND | YES | FEMALE | 76 | YES |
| 101069 | PD | ND | 94 | NO | ND | YES | MALE | 81 | YES |
| 101075 | HI | ND | 659 | YES | YES | YES | MALE | 71 | YES |

TABLE 2-continued

| SUBJID | RESPONSE | N-Ras Mutation | OS | Alive | Microarray | qPCR | SEX | AGE | Prior MDS |
|---|---|---|---|---|---|---|---|---|---|
| 101077 | SD | ND | 574 | YES | YES | ND | FEMALE | 75 | YES |
| 101078 | PD | ND | 190 | NO | ND | YES | FEMALE | 77 | NO |
| 101079 | PD | ND | 429 | NO | ND | YES | FEMALE | 70 | YES |
| 101083 | PD | ND | 71 | NO | ND | YES | MALE | 73 | YES |
| 101091 | CR | ND | 671 | YES | ND | YES | MALE | 71 | YES |
| 101092 | PD | ND | 136 | NO | ND | YES | FEMALE | 69 | YES |
| 101094 | HI | ND | 579 | YES | ND | YES | MALE | 65 | YES |
| 101095 | PD | ND | 108 | NO | YES | YES | MALE | 82 | YES |
| 101096 | CR | ND | 390 | YES | ND | YES | MALE | 69 | YES |
| 101101 | PD | ND | 91 | NO | ND | YES | MALE | 69 | YES |
| 101102 | PD | ND | 76 | NO | YES | YES | MALE | 69 | YES |
| 101103 | PD | ND | 29 | NO | ND | YES | FEMALE | 80 | NO |
| 101108 | PR | ND | 123 | NO | NO | YES | MALE | 70 | YES |
| 101109 | SD | ND | 656 | YES | YES | ND | MALE | 68 | YES |
| 101114 | PD | ND | 69 | NO | YES | YES | MALE | 72 | YES |
| 101121 | PD | ND | 43 | NO | ND | YES | MALE | 78 | NO |
| 101122 | PD | ND | 44 | NO | ND | YES | FEMALE | 80 | NO |

ND = not determined; WT = wildtype; CR = complete response; PR = partial response; HI = hematological improvement, SD = stable disease, PD = progressive disease, OS = Overall survival.

Identification of Predictive Genes from the Newly Diagnosed AML Cohort

We next aimed to identify genes predictive of response to tipifarnib in the newly diagnosed AML population. To this end we performed discovery experiments in the 13 responders (9 CR and 4 HI) and 13 patients with progressive disease. Patients with stable disease were not utilized in this analysis since these patients cannot be clearly defined as either responders or non-responders. Using the same approach as was utilized for identifying markers for relapsed and refractory AML (20070048782) we identified 45 probesets (corresponding to 38 unique genes) that were predictive of response (Table 3). The selection criteria aimed at identifying genes that would predict responders with a high sensitivity (approaching 100%) with a specificity cut-off of 40% and a mean gene expression difference of at least two-fold. The genes were ranked based on the area under the curve (AUC) defined from a receiver operator characteristic (ROC) analysis of the training set. This value represents the overall predictive value of the gene with an AUC of 1.0 indicating perfect classification. Each gene was first tested on the training set using a LOOCV method. The top gene, the RAS guanyl-releasing protein 1 (RASGRP1), showed an AUC of 0.95.

TABLE 3

45 probesets predictive of response to tipifarnib in newly diagnosed AML

| Probe Set ID | Gene Symbol | Gene Title | pvalue | spec | tstat | FC | AUC |
|---|---|---|---|---|---|---|---|
| 205590_at | RASGRP1 | RAS guanyl releasing protein 1 | 2.64E-06 | 0.54 | 6.40 | 4.01 | 0.95 |
| 217028_at | CXCR4 | chemokine (C—X—C motif) receptor 4 | 4.41E-05 | 0.69 | 5.08 | 2.35 | 0.92 |
| 206687_s_at | PTPN6 | protein tyrosine phosphatase, non-receptor type 6 | 8.23E-05 | 0.77 | -4.75 | -2.15 | 0.91 |
| 210439_at | ICOS | inducible T-cell co-stimulator | 1.27E-04 | 0.77 | 4.56 | 3.81 | 0.91 |
| 206641_at | TNFRSF17 | tumor necrosis factor receptor superfamily, member 17 | 3.79E-02 | 0.62 | 2.24 | 2.55 | 0.91 |
| 213539_at | CD3D | CD3d molecule, delta (CD3-TCR complex) | 1.75E-04 | 0.69 | 4.63 | 2.82 | 0.91 |
| 208018_s_at | HCK | hemopoietic cell kinase | 2.62E-04 | 0.62 | -4.28 | -3.14 | 0.90 |
| 203063_at | PPM1F | protein phosphatase 1F (PP2C domain containing) | 3.66E-04 | 0.85 | -4.17 | -2.31 | 0.90 |
| 208130_s_at | TBXAS1 | thromboxane A synthase 1 | 2.70E-04 | 0.46 | -4.26 | -2.51 | 0.89 |
| 216834_at | RGS1 | regulator of G-protein signalling 1 | 3.90E-04 | 0.62 | 4.16 | 3.48 | 0.87 |
| 213388_at | PDE4DIP | phosphodiesterase 4D interacting protein (myomegalin) | 1.47E-03 | 0.54 | -3.64 | -2.01 | 0.86 |
| 38487_at | STAB1 | stabilin 1 | 7.95E-04 | 0.54 | -3.87 | -2.45 | 0.86 |
| 210982_s_at | HLA-DRA | major histocompatibility complex, class II, DR alpha | 4.23E-03 | 0.69 | -3.25 | -3.07 | 0.85 |
| 210321_at | GZMH | granzyme H (cathepsin G-like 2, protein h-CCPX) | 1.64E-03 | 0.54 | 3.55 | 2.83 | 0.85 |
| 217147_s_at | TRAT1 | T cell receptor associated transmembrane adaptor 1 | 1.19E-03 | 0.54 | 3.72 | 2.82 | 0.85 |
| 206298_at | ARHGAP22 | Rho GTPase activating protein 22 | 7.89E-04 | 0.62 | -3.88 | -2.19 | 0.85 |
| 202990_at | PYGL | phosphorylase, glycogen; liver | 1.95E-03 | 0.46 | -3.50 | -2.01 | 0.85 |
| 221671_x_at | IGKC | immunoglobulin kappa constant | 1.62E-03 | 0.46 | 3.56 | 3.10 | 0.85 |
| 221651_x_at | IGKC | immunoglobulin kappa constant | 1.65E-03 | 0.46 | 3.57 | 2.92 | 0.85 |
| 207651_at | GPR171 | G protein-coupled receptor 171 | 1.13E-03 | 0.62 | 3.70 | 3.01 | 0.85 |
| 202988_s_at | RGS1 | regulator of G-protein signalling 1 | 1.48E-03 | 0.54 | 3.59 | 2.95 | 0.84 |
| 213418_at | HSPA6 | heat shock 70 kDa protein 6 | 1.63E-02 | 0.62 | -2.61 | -2.34 | 0.83 |
| 209901_x_at | AIF1 | allograft inflammatory factor 1 | 3.52E-03 | 0.54 | -3.24 | -2.48 | 0.83 |
| 205488_at | GZMA | granzyme A | 4.43E-03 | 0.46 | 3.18 | 2.75 | 0.83 |
| 217022_s_at | IGHA1 | immunoglobulin heavy constant alpha 1 | 3.43E-03 | 0.69 | 3.36 | 2.56 | 0.83 |
| 207339_s_at | LTB | lymphotoxin beta (TNF superfamily, member 3) | 1.34E-03 | 0.46 | 3.65 | 2.40 | 0.83 |
| 206337_at | CCR7 | chemokine (C—C motif) receptor 7 | 1.14E-03 | 0.54 | 3.71 | 2.08 | 0.83 |
| 208894_at | HLA-DRA | major histocompatibility complex, class II, DR alpha | 6.14E-03 | 0.46 | -3.05 | -2.58 | 0.82 |
| 39729_at | PRDX2 | peroxiredoxin 2 | 5.81E-03 | 0.54 | 3.05 | 2.13 | 0.82 |
| 209500_x_at | TNFSF13 | tumor necrosis factor (ligand) superfamily, member 13 | 1.23E-03 | 0.46 | -3.68 | -2.02 | 0.82 |
| 214677_x_at | IGL@ | immunoglobulin lambda locus | 4.69E-03 | 0.46 | 3.17 | 2.86 | 0.82 |
| 210314_x_at | TNFSF13 | tumor necrosis factor (ligand) superfamily, member 13 | 3.48E-03 | 0.46 | -3.24 | -2.05 | 0.81 |
| 209138_x_at | IGL@ | Immunoglobulin lambda locus | 4.17E-03 | 0.54 | 3.17 | 3.41 | 0.80 |
| 207831_x_at | DHPS | deoxyhypusine synthase | 1.09E-02 | 0.62 | -2.77 | -2.05 | 0.80 |
| 215121_x_at | IGL@ | immunoglobulin lambda locus | 1.20E-02 | 0.46 | 2.72 | 4.42 | 0.79 |

TABLE 3-continued 45 probesets predictive of response to tipifarnib in newly diagnosed AML

| Probe Set ID | Gene Symbol | Gene Title | pvalue | spec | tstat | FC | AUC |
|---|---|---|---|---|---|---|---|
| 215946_x_at | CTA-246H3.1 | similar to omega protein | 1.10E−02 | 0.46 | 2.76 | 2.46 | 0.79 |
| 204069_at | MEIS1 | Meis1, myeloid ecotropic viral integration site 1 homolog | 1.01E−02 | 0.62 | −2.89 | −2.14 | 0.78 |
| 204698_at | ISG20 | interferon stimulated exonuclease gene 20 kDa | 6.93E−03 | 0.46 | 2.95 | 2.39 | 0.78 |
| 209906_at | C3AR1 | complement component 3a receptor 1 | 1.49E−02 | 0.54 | −2.65 | −2.05 | 0.77 |
| 205608_s_at | ANGPT1 | angiopoietin 1 | 6.40E−03 | 0.46 | −3.11 | −2.18 | 0.76 |
| 205927_s_at | CTSE | cathepsin E | 2.02E−02 | 0.46 | 2.55 | 2.05 | 0.76 |
| 215051_x_at | AIF1 | allograft inflammatory factor 1 | 1.54E−02 | 0.62 | −2.62 | −2.03 | 0.76 |
| 205609_at | ANGPT1 | angiopoietin 1 | 4.12E−02 | 0.54 | −2.20 | −3.11 | 0.73 |
| 202890_at | MAP7 | microtubule-associated protein 7 | 3.30E−02 | 0.62 | −2.30 | −2.31 | 0.73 |
| 203485_at | RTN1 | reticulon 1 | 2.60E−02 | 0.54 | −2.40 | −2.29 | 0.72 |

Spec = specificity, FC = fold change, AUC = area under the curve of Receiver Operator Characteristic Analysis, negative t-statistic indicates gene is down in responders.

We then examined whether increasing the number of genes in the classifier improved its predictive value. Using the LOOCV approach and then plotting sensitivity, specificity, and overall error rate of each classifier, it was found that the top gene alone provided the best predictive value (data not shown). Adding genes to the classifier in a linear fashion did not improve its predictive value. Using a cutoff that biases for high sensitivity, the LOOCV demonstrated that the expression of the RASGRP1 gene allowed for a NPV 88.9%, and a PPV of 70.6%, with an overall predictive accuracy of 76.9% (FIG. 1A). In addition, Kaplan Meier analysis showed a significant difference in median overall survival of the responders (386 days) and those with progressive disease (68 days) (FIG. 1B). Over expression of this single gene therefore predicted response to tipifarnib in newly diagnosed AML with a high negative predictive value.

Identification of a Top Scoring Pair classifier

The predictive value of RASGRP1 was not improved if additional genes were added to the classifier using a linear approach. We thus utilized an alternative gene selection algorithm to select genes that would improve the predictive value of RASGRP1 alone. To this end we utilized the Top Scoring Pair (TSP) algorithm to identify the best pair of genes that would provide the greatest predictive accuracy. Geman et al. (2004). This approach was utilized to exploit the greatest difference in expression between two genes and may be useful when aiming to develop a qPCR based diagnostic assay. The TSP from the training set was RASGRP1 and aprataxin (APTX). RASGRP1 and APTX were over- and under-expressed in responders, respectively. A robust LOOCV showed that this top scoring pair (TSP) provided 85.7% NPV and 91.7% PPV in the training set of samples with an overall error rate of only 8% (FIG. 2A). The difference in overall survival between predicted responders and non-responders was 357 days (FIG. 2B). These data demonstrate that the model-building algorithm has a low associated prediction error rate.

Validation of the RASGRP1:APTX Classifier in an Independent Set of Relapsed or Refractory AML.

We next performed external validation of the TSP classifier in an independent microarray dataset comprising of 54 relapsed/refractory AML patient samples. 20070048782. Importantly, a diagnostic assay that aims to predict response to a cancer therapy should have a high sensitivity (and negative predictive value) since it is important to capture as many potential responders as possible. Therefore, to define an appropriate cutoff for testing the TSP classifier we considered the need to obtain a high sensitivity of predicting responders while maintaining an acceptable level of specificity. In the training set, the level of specificity that could be achieved ranged from approximately 30% to 100% when the sensitivity was set at 100% to 80%, respectively. To ensure the classifier would predict as many responders as possible we tested a conservative cutoff that provided a specificity of approximately 60% in the training set. When this cutoff was applied to the independent testing set of relapsed/refractory AML, the RASGRP1:APTX gene classifier stratified responders with 92% NPV and 27.6% PPV (compared to 18.5% prevalence) (FIG. 3C). The associated odds ratio for being a responder was 4.38. While this was similar to the predictive accuracy of RASGRP1 alone, the application of the TSP classifier demonstrated a better NPV and an improved difference in overall survival of 98 days between predicted responders and progressors, compared to only 56 days for RASGRP1 (FIG. 4).

QPCR Validation of the RASGRP1:APTX Expression Ratio

Figure 6:
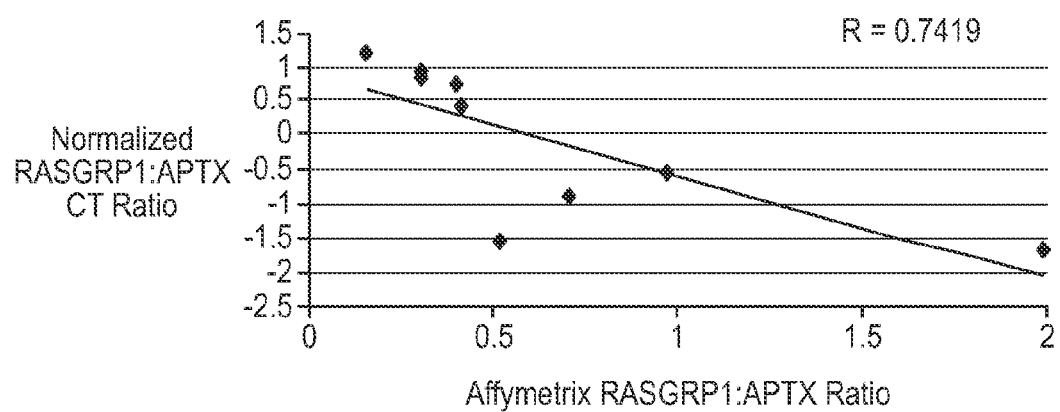
FIG. 6 depicts the correlation of Affymetrix and qPCR data. Nine RNA samples that were analyzed on both the Affymetrix GeneChip and by qPCR were compared by linear regression analysis.

A two-gene expression ratio allows the use of a more clinically relevant qPCR detection system. Thirty samples (20 PD, 6 CR, 3 HI and 1 PR) provided enough total RNA for qPCR. Therefore, the RASGRP1:APTX gene expression ratio was evaluated as a predictor of response to tipifarnib using TaqMan® qPCR in these 30 samples (10 responders, 20 progressive disease) from the newly diagnosed AML clinical study. Nine of these samples had been assayed on the microarray platform, however 21 had not been utilized in the discovery set due to poor quality RNA. Therefore, two thirds of this test set was comprised of completely independent samples. Evaluation of the 9 samples indicated there was good correlation (r=0.74) of the RASGRP1:APTX expression ratio between the two platforms (FIG. 6). Using a cut-point of 0, the two-gene classifier correctly predicted the treatment outcome in 20 of the 30 patients with PPV and NPV of 50% and 81%, respectively (FIG. 3). The median overall survival of the predicted resistant patients was 82 days while those classified as responders had a median value of 295 days (FIG. 3C).

The RASGRP1:APTX Classifier does not have Prognostic Utility Independent of FTI Treatment.

Figure 5:
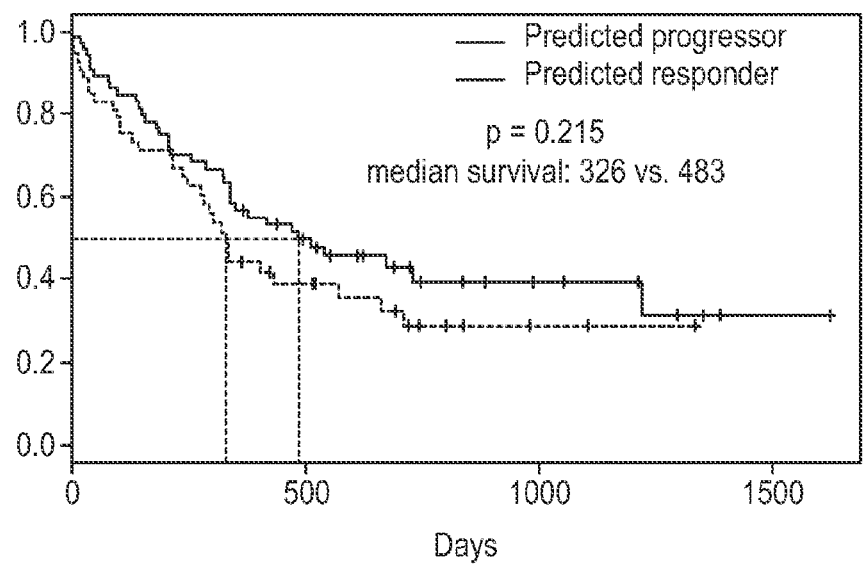
FIG. 5 depicts the overall survival of non-FTI treated AML patients stratified with the RASGRP1:APTX gene expression ratio. Three cDNA probes for both RASGRP1 and APTX were present in the available data set. We first calculated the mean value for each gene and then calculated the RASGRP1:APTX ratio of these values. Patients whose ratio was above 1 were classified as progressors and those with a ratio below 1 were classified as responders. Kaplan-Meier analysis was then performed.

We tested the two-gene expression ratio in an independent microarray dataset of 116 AML patients treated with chemotherapeutic regimes. Bullinger et al. (2004). When the RASGRP1:APTX classifier was applied to this set of patients, utilizing a similar cut-off as for the tipifarnib-treated population, no significant separation in overall survival was seen (FIG. 5). Nor were significant survival differences observed when a range of other cut-offs was utilized (Table 4). This indicated that the RASGRP1:APTX classifier specifically stratifies patients who have been treated with tipifarnib and is not relevant to non-FTIs. On the other hand when the prognostic signature defined by Bullinger et al. was applied to our set of relapsed and refractory AML patients there was a clear stratification in terms of overall survival.

TABLE 4

| cutoff | p value | Responders median OS | Progressors median OS | No. Responders | No. Progressors |
|---|---|---|---|---|---|
| 0.5 | 0.956 | 336 | 414 | 13 | 103 |
| 0.6 | 0.342 | 672 | 374 | 24 | 92 |
| 0.7 | 0.266 | 511 | 335 | 34 | 82 |
| 0.8 | 0.269 | 511 | 326 | 47 | 69 |
| 0.9 | 0.101 | 540 | 316 | 57 | 59 |
| 1 | 0.215 | 483 | 326 | 64 | 52 |
| 2 | 0.795 | 374 | 570 | 94 | 22 |
| 3 | 0.209 | 346 | 909 | 104 | 12 |

Figures 2C, 2D:
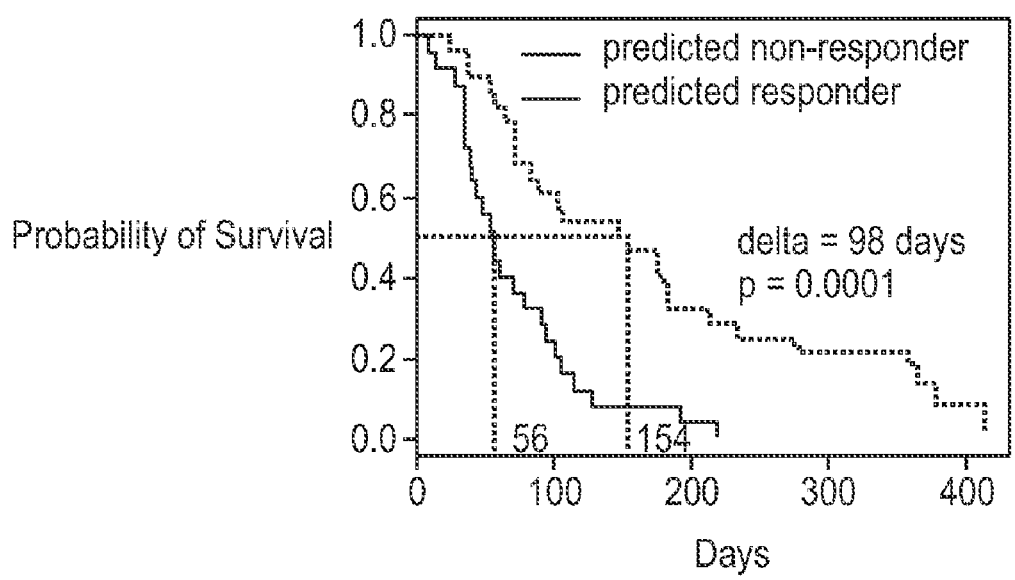

OS = overall survival
Kaplan-Meier analysis is shown in Supplementary FIG. 2 for highlighted (bold) cut-off.

DISCUSSION

Stratification of patient populations to predict therapeutic response is becoming increasingly valuable in the clinical management of cancer patients. For example, companion diagnostics are required for the stratification of patients being treated with targeted therapies such as trastuzumab (Herceptin, Genentech) in metastatic breast cancer, and cetuximab (Erbitux, Merck) in colorectal cancer. Seidman et al. (2001); and Moroni et al. (2005). Predictive biomarkers are also being utilized for imatinib (Gleevec, Novartis) in gastrointestinal stromal tumors, and for erlotinib (Tarceva, OSI Pharmaceuticals) and gefitinib (Iressa, Astra-Zeneca) in lung cancer. Burger et al. (2005); Tsao et al. (2005); and Lynch et al. (2004). Currently there is no method available to predict response to an FTI in any indication. To identify genes that are associated with greater sensitivity to the FTI, tipifarnib, we performed gene expression profiling of leukemic bone marrow samples from a phase 2 study in elderly patients with previously untreated poor-risk AML. Lancet et al. (2006). Importantly, an assay that aims to predict response to an oncology therapy should have a high NPV since it is important to capture as many potential responders as possible. Therefore, using criteria to identify markers that predict response with high sensitivity, we identified 45 genes in the newly diagnosed AML bone marrow samples that were differentially expressed between responders and non-responders.

While we found no significant correlation with N-Ras mutations or baseline phosphorylation status of ERK or AKT and response to tipifarnib (Lancet et al. (2006)), we did identify genes predictive of response to tipifarnib that are involved in Ras activation including, PTPN6 (a protein tyrosine phosphatase that is farnesylated and was down-regulated in responders), CD3D, TRAT1, LTB, TNFRSF17, TNFSF13, and RASGRP1. Chen et al. (2005); Stone (2006); and Delgado (2000). It is well known that activation of the Ras pathway can be caused by other events outside of constitutive activation of the Ras protein itself. Illmer et al. (2005); and Solit et al. (2006). Indeed, N-Ras and K-Ras have been identified in their activated state in AML in the absence of activating mutations. Ehmann et al. (2006). It is therefore plausible that Ras deregulation is an important target of tipifarnib in AML regardless of Ras mutational status. Watters et al. (2006). In support of this, Feldkamp et al. (2001) demonstrated that isotype-specific Ras.GTP levels correlates with response to the FTI SCH66336 regardless of Ras activating mutations.

RASGRP1 was the most robust single predictive gene expression marker with an overall predictive accuracy of 77% in the cross-validated training set. RASGRP1 is a guanine nucleotide exchange factor (GEF) that specifically activates Ras. Stone (2006). Expression of RASGRP1 has been found in brain, T-cells, cells of monocytic lineage, and primitive hematopoietic precursors. Kawasaki et al. (1998) Ebinu et al. (1998); and Tognon et al. (1998). Interestingly, another RAS-GRP (RASGRP4) was previously identified as a potential oncogene in AML (Reuther et al. (2002)), however, our data is the first to examine and demonstrate expression of RAS-GRP1 in AML cells in addition to implicating it's importance in response to FTIs.

We found that the combination of RASGRP1 and APTX provided the most robust predictive accuracy (approximately 89%) for a multi-gene classifier. APTX is involved in DNA excision repair and was found to be down-regulated in responders. Ahel et al. (2006). This two-gene classifier showed predictive utility in the discovery set of newly diagnosed AML when a cross validation was performed, with a NPV and PPV of identifying responders of 86% and 92%, respectively. However, cross-validation only provides a model of performance and thus testing of an independent data set was performed to provide bona fide accuracy of response prediction. To this end we also examined microarray data from an independent set of relapsed/refractory AML and performed qPCR on independent samples from the newly diagnosed AML clinical study.

A simple qPCR-based diagnostic assay has wider utility in the clinic than gene expression microarrays due to the ability to assay poor quality clinical samples that may not be profiled by current microarray technologies. In a set of 30 samples (20 of which had not been profiled by microarray) from the newly diagnosed AML population, we demonstrated that the RASGRP1:APTX expression ratio can be reliably detected with qPCR regardless of sample quality. The classifier demonstrated a NPV and PPV of 81% and 50%, respectively and provided a clear overall survival advantage for those patients predicted to be responders. Clearly, it will be important to profile larger datasets in future studies to further validate the use of a two-gene qPCR assay.

In the absence of a larger independent set of newly diagnosed AML samples we also utilized 54 relapsed or refractory AML samples from our previous investigation as an independent testing set (20070048782). Surprisingly, even though the samples were from a biologically distinct population of AML patients the two-gene classifier showed good stratification of responders and non-responders with a NPV of 92% and a PPV of 28%. Since the prevalence of responders in that dataset was 18% this represents an improvement of overall response of approximately 50%. Furthermore, the stratified predicted responders had a median overall survival that was approximately 3-fold longer than patients predicted to be resistant to tipifarnib. Importantly we found no association with the two-gene classifier and patient prognosis in an independent set of AML patients who were treated with chemotherapeutics. This indicated that the current classifier specifically predicts response to tipifarnib treatment. Further work needs to be done to clarify whether the RASGRP1:APTX expression ratio has utility for other classes of FTIs.

How might increased RASGRP1 expression lead to sensitivity to FTIs? RASGRP1 has been shown to activate H-RAS and N-Ras, but not K-Ras, exclusively on the golgi apparatus. Bivona et al. (2003); and Perez de Castro et al. (2004). Further, K-Ras and N-Ras can be alternatively geranylgeranylated following farnesyltransferase inhibition. Whyte et al. (1997). H-Ras on the other hand is only farnesylated and this may explain the observation that tumors transformed with H-Ras are more sensitive than those transformed with N-, or K-Ras. End et al. (2001); and Lubet et al. (2006). Thus it is possible that aberrant expression of RASGRP1 in AML leads to activation of the N-Ras and H-Ras pathways but it is the blockage of H-Ras that is causing the anti-tumorigenic effect. Therefore, while H-Ras activating mutations have not been identified in AML, the specific activation of H-Ras pathways by other means (such as Ras-specific GEFs) may still be a target of FTIs in certain tumors.

We previously identified AKAP13 as being predictive of resistance to tipifarnib in relapsed/refractory AML. 200700448782. Interestingly, AKAP13 is also a GEF, but activates the Rho pathway. Sterpetti et al. (1999). However, whilst showing utility in relapsed or refractory AML, expression of AKAP13 did not demonstrate predictive utility in newly diagnosed AML. This may be because the population of leukemic cells that over-express AKAP13 is absent in newly diagnosed disease and only proliferates in late stage AML. The other question that arises is why over-expression of the RASGRP1 GEF increases sensitivity while over-expression of the AKAP13 GEF increases resistance to tipifarnib? Rho GEFs have been found to drive cellular transformation in a Ras-independent fashion. Reuther et al. (2001); and Sahai et al. (2002). Thus, one hypothesis is that AKAP13 activates a downstream compensatory pathway in RhoA while RAGRP1 activates Ras, a clear target of FTIs. More biochemical analyses will need to be done to investigate this model. Nevertheless, the identification of two GEFs playing opposing roles in responsiveness to an FTI does highlight the importance of this class of small GTPase activators in FTI-mediated therapy. It also highlights the need for multiple markers in predicting response to targeted therapies across a wide range of diseases and disease subtypes. As GEFs are increasingly becoming attractive drug targets it may also be of interest to investigate combination therapies of FTIs and inhibitors of specific GEFs.

In summary, we have identified and validated a two-gene expression ratio that can be assayed using simple qPCR. The classifier has predictive utility in both newly diagnosed and relapsed or refractory AML, and improves the overall response rate by approximately 50% while maintaining a high NPV. In addition, stratification with this classifier significantly improves patient overall survival. Our data compare favorably to the use of FDA-approved companion diagnostics for targeted cancer therapies such as Herceptin. For instance, it has been demonstrated that stratification of metastatic breast cancer patients with over-expression of Her2/Neu improves the overall response to Herceptin and paclitaxel combination therapy from approximately 59% to 69% or 75% when using the HercepTest or PathVysion tests, respectively. Seidman et al. (2001). Our data therefore indicates that a simple two-gene expression assay may have utility in diagnosing a population of AML patients who are more likely to respond to tipifarnib.

REFERENCES

Ahel et al. (2006) The neurodegenerative disease protein aprataxin resolves abortive DNA ligation intermediates Nature 443:713-716

Bivona et al. (2003) Phospholipase Cgamma activates Ras on the Golgi apparatus by means of RasGRP1 Nature 424:694-698

Bos (1989) ras oncogenes in human cancer: a review Cancer Res 49:4682-4689

Bullinger et al. (2004) Use of gene-expression profiling to identify prognostic subclasses in adult acute myeloid leukemia N Engl J Med 350:1605-1616

Burger et al. (2005) Activating mutations in c-KIT and PDG-FRalpha are exclusively found in gastrointestinal stromal tumors and not in other tumors overexpressing these imatinib mesylate target genes Cancer Biol Ther 4:1270-1274

Chang et al. (2003) Gene expression profiling for the prediction of therapeutic response to docetaxel in patients with breast cancer Lancet 362:362-369

Chen et al. (2005) FLT3/ITD mutation signaling includes suppression of SHP-1 J Biol Chem 280:5361-5369

Cox et al (2002) Farnesyltransferase inhibitors: promises and realities Curr Opin Pharmacol 2:388-393

Ebinu et al. (1998) RasGRP, a Ras guanyl nucleotide-releasing protein with calcium- and diacylglycerol-binding motifs Science 280:1082-1086

Ehmann et al. (2006) Detection of N-RAS and K-RAS in their active GTP-bound form in acute myeloid leukemia without activating RAS mutations Leuk Lymphoma 47:1387-1391

End et al. (2001) Characterization of the antitumor effects of the selective farnesyl protein transferase inhibitor R115777 in vivo and in vitro Cancer Res 61:131-137

Feldkamp et al. (2001) Isotype-specific RasGTP-levels predict the efficacy of farnesyl transferase inhibitors against human astrocytomas regardless of Ras mutational status Cancer Res 61:4425-4431

Geman et al. (2004) Classifying gene expression profiles from pairwise mRNA comparisons Stat Appl Genet Mol Biol 3:30

Holleman et al. (2004) Gene-expression patterns in drug-resistant acute lymphoblastic leukemia cells and response to treatment N Engl J Med 351:533-542

Illmer et al. (2005) Activation of the RAS pathway is predictive for a chemosensitive phenotype of acute myelogenous leukemia blasts Clin Cancer Res 11:3217-322

Jansen et al. (2005) Molecular classification of tamoxifen-resistant breast carcinomas by gene expression profiling J Clin Oncol 23:732-740

Karp et al. (2001) Clinical and biologic activity of the farnesyltransferase inhibitor R115777 in adults with refractory and relapsed acute leukemias: a phase 1 clinical-laboratory correlative trial Blood 97:3361-3369

Kawasaki et al. (1998) A Rap guanine nucleotide exchange factor enriched highly in the basal ganglia Proc Natl Acad Sci 95:13278-13283

Lancet et al. (2006) A phase II study of the farnesyltransferase inhibitor tipifarnib in poor-risk and elderly patients with previously untreated acute myelogenous leukemia Blood 2:2

Lossos et al. (2004) Prediction of survival in diffuse large-B-cell lymphoma based on the expression of six genes N Engl J Med 350:1828-1837

Lubet et al. (2006) Effects of the farnesyl transferase inhibitor R115777 (Zarnestra) on mammary carcinogenesis: prevention, therapy, and role of HaRas mutations Mol Cancer Ther 5:1073-1078

Lynch et al. (2004) Activating mutations in the epidermal growth factor receptor underlying responsiveness of non-small-cell lung cancer to gefitinib N Engl J Med 350:2129-2139

Ma et al. (2004) A two-gene expression ratio predicts clinical outcome in breast cancer patients treated with tamoxifen Cancer Cell 5:607-616

Mesa et al (2006) Tipifarnib: farnesyl transferase inhibition at a crossroads Expert Rev Anticancer Ther 6:313-319

Moroni et al. (2005) Gene copy number for epidermal growth factor receptor (EGFR) and clinical response to antiEGFR treatment in colorectal cancer: a cohort study Lancet Oncol 6:279-286

Perez de Castro et al. (2004) A Ras activation in Jurkat T cells following low-grade stimulation of the T-cell receptor is specific to N-Ras and occurs only on the Golgi apparatus Mol Cell Biol 24:3485-3496

Potti et al. (2006) Genomic signatures to guide the use of chemotherapeutics Nat Med 12:1294-1300

Rao et al. (2004) Phase III Double-Blind Placebo-Controlled Study of Farnesyl Transferase Inhibitor R115777 in Patients With Refractory Advanced Colorectal Cancer J Clin Oncol 22:3950-3957

Reuter et al. (2000) Targeting the Ras signaling pathway: a rational, mechanism-based treatment for hematologic malignancies? Blood 96:1655-1669

Reuther et al. (2001) Leukemia-associated Rho guanine nucleotide exchange factor, a Dbl family protein found mutated in leukemia, causes transformation by activation of RhoA J Biol Chem 276:27145-27151

Reuther et al. (2002) RasGRP4 is a novel Ras activator isolated from acute myeloid leukemia J Biol Chem 277: 30508-30514

Rosenwald et al. (2002) The use of molecular profiling to predict survival after chemotherapy for diffuse large-B-cell lymphoma N Engl J Med 346:1937-1947

Rowinsky et al (1999) Ras protein farnesyltransferase: A strategic target for anticancer therapeutic development J Clin Oncol 17:3631-3652

Sahai et al. (2002) RHO-GTPases and cancer Nat Rev Cancer 2:133-142

Seidman et al. (2001) Weekly trastuzumab and paclitaxel therapy for metastatic breast cancer with analysis of efficacy by HER2 immunophenotype and gene amplification J Clin Oncol 19:2587-2595

Ship et al. (2002) Diffuse large B-cell lymphoma outcome prediction by gene-expression profiling and supervised machine learning Nat Med 8:68-74

Solit et al. (2006) BRAF mutation predicts sensitivity to MEK inhibition Nature 439:358-362

Sterpetti et al. (1999) Activation of the Lbc Rho exchange factor proto-oncogene by truncation of an extended C terminus that regulates transformation and targeting Mol Cell Biol 19:1334-1345

Stone (2006) Regulation of Ras in lymphocytes: get a GRP Biochem Soc Trans 34:858-861

Tognon et al. (1998) Regulation of RasGRP via a phorbol ester-responsive C1 domain Mol Cell Biol 18:6995-7008

Tsao et al. (2005) Erlotinib in lung cancer—molecular and clinical predictors of outcome N Engl J Med 353:133-144

Van Cutsem et al. (2004) Phase III trial of gemcitabine plus tipifarnib compared with gemcitabine plus placebo in advanced pancreatic cancer J Clin Oncol 22:1430-1438

Waters et al. (2006) Developing gene expression signatures of pathway deregulation in tumors Mol Cancer Ther 5:2444-2449

Weinstein et al. (2006) Mechanisms of disease: Oncogene addiction—a rationale for molecular targeting in cancer therapy Nat Clin Pract Oncol 3:448-457

White et al. (1997) K- and N-Ras are geranylgeranylated in cells treated with farnesyl protein transferase inhibitors J Biol Chem 272:14459-14464

Yeoh et al. (2002) Classification, subtype discovery, and prediction of outcome in pediatric acute lymphoblastic leukemia by gene expression profiling Cancer Cell 1:133-143

Sequences
Probe Set ID

205590_at

```
ggattcaaaaggtgtcacagtccacttaattagtcaaattagcaatggctaaacagtatcaagtactgcagaattt
atcactgaaatggataagaggaaatagtttagtcacaggttttacagtccagcaagggccaaagaggtatagt
atacaagttaatagtatttgtgttgagcaacatggggctagtgggatcacagaaatctggaaaaaaaaaaaaa
aaggctttggcttatcaagcctagtgtaaatttctgcatctcacacgactttagtttggccaggtatttatctgccaaa
acaaggacaaatcttgttgtattaacagcagggtcacttctcattttctttgctgacttaccttttttactgaccgttgtga
atttctgtctcaaa
```

217028_at

```
attgatgtgtgtctaggcaggacctgtggccaagttcttagttgctgtatgtctcgtggtaggactgtagaaaaggg
aactgaacattccagagcgtgtagtgaatcacgtaaagctagaaatgatcccagctgtttatgcatagataatct
ctccattcccgtggaacgttttctctgttcttaagacgtgattttgctgtagaagatggcacttataaccaaagcccaa
agtggtatagaaatgctggttttcagttttcaggagtgggttgatttcagcacc
```

206687_s_at

```
gggcctggactgtgacattgacatccagaagaccatccagatggtgcgggcgcagcgctcgggcatggtgca
gacggaggcgcagtacaagttcatctacgtggccatcgcccagttcattgaaaccactaagaagaagctggag
gtcctgcagtcgcagaagggccaggagtcggagtacgggaacatcacctatccccagccatgaagaatgc
ccatgccaaggcctcccgcacctcgtccaaacacaaggaggatgtgtatgagaacctgcacactaagaacaa
gagggaggagaaagtgaagaagcagcggtcagcagacaaggagaagagcaagggttccctcaagagga
agtgagcggtgctgtcctcaggtggccatgcctcagccctgaccctgtggaagcatttcgcgatggacagactc
acaacctgaacctaggagtgcccc
```

210439_at

```
gcttctgaagcagccaatgtcgatgcaacaacatttgtaactttaggtaaactgggattatgttgtagtttaacatttt
gtaactgtgtgcttatagtttacaagtgagacccgatatgtcattatgcatacttatattatcttaagcatgtgtaatgct
ggatgtgtacagtacagtacttaacttgtaatttgaatctagtatggtgttctgttttcagctgacttggacaacctgact
ggctttgcacaggtgttccctgagttgtttgcaggtttctgtgtgtggggtggggtatgggaggagaaccttcatgg
tggcccacctggcctggttgtccaagctgtgcctcgacacatcctcatcccaagcatgggacacctcaagatga
ataataattcacaaaatttctgtgaaatcaaatccagtttttaagaggagccacttatcaaagagat
```

-continued

| Sequences |
| --- |
| Probe Set ID |

206641_at atttctttggcagttttcgtgctaatgttttgctaaggaagataagctctgaaccattaaaggacgagtttaaaaaca
caggatcaggtctcctgggcatggctaacattgacctggaaaagagcaggactggtgatgaaattattcttccga
gaggcctcgagtacacggtggaagaatgcacctgtgaagactgcatcaagagcaaaccgaaggtcgactct
gaccattgctttccactcccagctatggaggaaggcgcaaccattcttgtcaccacgaaaacgaatgactattgc
aagagcctgccagctgctttgagtgctacggagatagagaaatcaatttctgctaggtaattaaccatttcgactc
gagcagtgccactttaaaaatcttttgtcagaatagatgatgtgtcagatctctttaggatgactgtatttttcagttgcc
gatacagcttttgtcctctaactg 213539_at gggaacactgctctcagacattacaagactggacctgggaaaacgcatcctggacccacgaggaatatatag
gtgtaatgggacagatatatacaaggacaaagaatctaccgtgcaagttcattatcgaatgtgccagagctgtgt
ggagctggatccagccaccgtggctggcatcattgtcactgatgtcattgccactctgctccttgctttgggagtcttc
tgctttgctggacatgagactggaaggctgtctggggctgccgcacacacaagctctgttgaggaatgaccaggt
ctatcagcccctccgagatcgagatgatgctcagtacagccaccttggaggaaactgggctcggaacaagtga
acctgagactggtggcttctagaagcagccattaccaactgtacct 208018_s_at gctgatggagatcgtcacctacggccggatcccttacccagggatgtcaaaccctgaagtgatccgagctctgg
agcgtggataccggatgcctcgccccagagaactgcccagaggagctctacaacatcatgatgcgctgctgga
aaaaccgtccggaggagcggccgaccttcgaatacatccagagtgtgctggatgacttctacacggccacag
agagccagtaccaacagcagccatgatagggaggaccagggcagggcaggggtgcccaggtggtggct
cgaaggtggctccagcaccatccgccagggcccacacccccttcctactcccagacacccaccctcgcttcag
ccacagtttcctcatctgtccagtgggtaggttggactggaaaatctcttttttgactcttgcaatccacaatctgacatt
ctcaggaagcccccaagttgatatttctatt 203063_at ctcagaatcccagaggcagtcccagcctcagaacccaggataggaaatgggtgtgtttagtggggaaaggga
cggggtgcagacggcagggccagtatggggccccctccctctcctctcctctcctatggtgagcccagcgtggg
caccgggccgtctcagccgtgttcccagggctgggaggacagctctggccttcttaggcctagcctcgtcccaa
gctaaatgtaagccagttgggctgtgttaaaggaagcagtgttttttgattctgcctctgtagctcaagggggg
cagcccccagagtcctgtgcattctgccaaggctccatagctttgccaaatgcacggagctctgccattccggtg
cagtgcaggccttgcgaagggtttatctgcgttcgtctcggtgggcttctcctgcatgggagttgtgttcctgtgcaag
ggggagctttgctcaggacaggatgactgtcttccctattcttagggacaagtcccaagatgccagaaaggcag
tctcccaagga 208130_s_at tatggccaggcctttgactgtggatgagattgtgggccaggccttcatcttcctcatcgctggctatgaaatcatcac
caacactttcttttgccacctacctactggccaccaacctgactgccaagagaagcttctgagagaggtaga
cgttttaaggagaaacacatggccctgagttctgcagcctcgaggaaggcctgccctatctggacatggtgatt
gcagagacgctgaggatgtacccgccagctttcagattcacacgggaggcagctcaggactgcgaggtgctg
gggcagcgcatccccgcaggcgctgtgctagagatggccgtgggtgccctgcaccatgaccctgagcactgg
ccaagcccggagaccttcaaccctgaaaggtaccgctgcagctagaatccaaatctgccctaggtccaaaaa
atggtgtctatatcaagatcgtatcccgctgacacagaaggctgccgg 216834_at atgaaactgattacaacaggctgtaagaatcaaagtcaactgacatctatgctacatattattatatagtttgtactg
agctattgaagtcccattaacttaaagtatatgttttcaaattgccattgctactattgcttgtcggtgtattttattttattgt
ttttgactttggaagagatgaactgtgtatttaacttaagctattgctcttaaaaccagggatcagaatatatttgtaag
ttaaatcattggtgctaataataaatgtggattttgtattaaaatatatagaagcaatttctgtttacatgtccttgctactt
ttaaaaacttgcatttattcctcagatttt 213388_at cctctttctcaatctataacctttgtaggcatgcatttataccagcatgttttataaattatgagtttctatctgtgtccatg
aagtcttactagttttcacttaaacttttgtgggttgttaagaagaattaaagtgattcataactttcacgcttgaacctg
ggaggtggaggttgcagtgagccgagatcatgccattgcactccagcctgggcaacaagagtgaaactctgtc
ttaaataaataaataaagtggttcataacatcagatgaagaaggaggtgagtgatatgttaaatgatcagaaact
tggcattacattattttccaggaccatttccctaccaaagctgtgtattttcatttcttcatggcactgtgctgttaatttctg
tta 38487_at acagttgtggttagccgtatcattgtgtgggacatcatggccttcaatggcatcatccatgctctggccagcccctc
ctggcacccccacagcccnagncagtgntggcgcctgaagcccccactgtggcggcaggcgnnnnnnnn
nnnnnnnnnnnnnncactgcttggcttggtggcggagctctctacctccgtgcccgaggcaagcccangg
gctttggcttctctgccttccaggcggaannnnnnnnnnnnnnnnnnnnnnnnngcaagaagggac
caaccccaccctggtctctgtccccaaccctgtctttggcagcgacaccttttgtgaaccttcgatgactcactgct
ggaggaggacttccctgacacccagaggatcctcacagtcaagt

| Sequences |
|---|
| Probe Set ID |

210982_s_at

```
gaaggagacggtctggcggcttgaagaatttggacgatttgccagctttgaggctcaaggtgcattggccaacat
agctgtggacaaagccaacttggaaatcatgacaaagcgctccaactatactccgatcaccaatgacaagttc
accccaccagtggtcaatgtcacgtggcttcgaaatggaaaacctgtcaccacaggagtgtcagagacagtctt
cctgcccagggaagaccacctttccgcaagttccactatctcccttcctgccctcaactgaggacgtttacgact
gcagggtggagcactgggcttggatgagcctcttctcaagcactgggagtttgatgctccaagccctctcccag
agactacagagaacgtggtgtgtgccctgggcctgactgtgggtctggtgggcatcattattgggaccatc
```

210321_at

```
gccaagtggaccacagctgtgcggcctctcaggctacctagcagcaaggcccaggtgaagccagggcagct
gtgcagtgtggctggctgggggttatgtctcaatgagcacttagcaaccacactgcaggaagtgttgctgacagtg
cagaaggactgccagtgtgaacgtctcttccatggcaattacagcagagccactgagatttgtgtggggggatcc
aaagaagacacagaccggtttcaagggggactccggggggcccctcgtgtgtaaggacgtagcccaaggta
ttctctcctatggaaataaaaaagggacacctccaggagtctacatcaaggtctcacacttcctgccctggataa
agagaacaatgaagcgcctctaacagcaggcatgagactaaccttcctctgggcctgaccatctctgggacag
aggcaagaatccccaagggtg
```

217147_s_at

```
tctcctttctcaccaatgggcaatagcccataattgaaataaatttctgattgaaaggtataggaaacattaaaatg
cattactaagagaagtaatataattttcttacaaagtattttcccaaagatagctttactatttcaaaaattgtcaaatt
aatgcatgctccttacaacaaacaaatatcaaaaagagtttaggaattctactagccagagatagtcacttggag
aaactttctatatatccttctaaatattttctgggcatgctcatgtatgtacatcagttgtttctttttattttgaaccaaaaa
tgtggtttcttttgtacacattact-
taaactttcttttccagtcaacaataatattgtggatttattttcactgttatatttaactata
tataaatacgcatatattgtaattttaatgtctgcttagcaccccactgataaccaaatcacag
```

206298_at

```
aagctgcggaactctgaacgggcgcgggaggatgcggagaggaggaaccagctgttgcagagggaaatg
gaggagttttttcgaccctaggaagcttgactgttggggcaaaaggtgccagggcccaaagtaaaaggaatg
gcagagctcacttctgtaccacgtctgctggtctccaggccttgtatggagttagaagcgtctgtatctctggagcag
ccaggcgctctggagccagctggagagagagagatcctgatacctctgtggggactgtggggacttttgggac
cccacacactccaggtgggatcagatgctgctccaaccatgcagttcctggtgagggtcagaaggggacggta
ccaagagcagcgcttagccccttacccaggaaatatccttcatggccacagaaatggagggcgcccaggatcc
aggcagccaccgggaacagtcagctttcttta
```

202990_at

```
agagcagatttccactgcaggcaccgaagcctcggggacaggcaatatgaagttcatgctaaatggggcccta
actatcgggaccatggatggggccaatgtggaaatggcagaagaagctggggaagagaacctgttcatctttg
gcatgaggatagatgatgtggctgctttggacaagaaagggtacgaggcaaaagaatactatgaggcacttcc
agagctgaagctggtcattgatcaaattgacaatggcttttttctcccaagcagcctgacctcttcaaagatatcat
caacatgctattttatcatgacaggtttaaagtctttgcagactacgaagcctatgtcaagtgtcaagataaagtga
gtcagctgtacatgaatccaaaggcctggaacacaatggtactcaaaaacatagctgcctcggggaaattctcc
agtgaccgaacaattaaagaatatgcccaaaacatctggaacgtggaaccttcagatctaaa
```

221671_x_at

```
caacaccgtgacaattggcctccgggggccactttcggcggagggaccaaggtggagatcaaacgaactgtg
gctgcaccatctgtcttcatcttcccgccatctgatgagcagttgaaatctggaactgcctctgttgtgtgcctgctga
ataacttctatcccagagaggccaaagtacagtggaaggtggataacgccctccaatcgggtaactcccagga
gagtgtcacagagcaggacagcaaggacagcacctacagcctcagcagcaccctgacgctgagcaaagc
agactacgagaaacacaaagtctacgcctgcgaagtcacccatcagggcctgagctcgcccgtcacaaaga
gcttcaacaggggagagtgttagagggagaagtgcccccacctgctcctcagttccagcctgacccctcccat
cctttggcctctgaccccttttccacaggggacctaccccattgcggtcctccagctcatctttcacctcacccccct
cctcctccttggctttaattatgc
```

221651_x_at

```
gttatcctgtcacttttggccaggggaccaagctggagatcaaacgaactgtggctgcaccatctgtcttcatcttc
ccgccatctgatgagcagttgaaatctggaactgcctctgttgtgtgcctgctgaataacttctatcccagagaggc
caaagtacagtggaaggtggataacgccctccaatcgggtaactcccaggagagtgtcacagagcaggaca
gcaaggacagcacctacagcctcagcagcaccctgacgctgagcaaagcagactacgagaaacacaaag
tctacgcctgcgaagtcacccatcagggcctgagctcgcccgtcacaaagagcttcaacaggggagagtgtta
gagggagaagtgcccccacctgctcctcagttccagcctgacccctcccatcctttggcctctgaccctttttcca
caggggacctaccccattgcggtcctccagctcatctttcacctcacccccctcctcctccttggctttaattatgc
```

207651_at

```
ttgccttgtaattcgacagctctacagaaacaaagataatgaaaatttacccaaatgtgaaaaaggctctcatcaa
catactttagtgaccacgggctacatcatatgctttgttccttaccacattgtccgaatcccgtataccctcagccag
acagaagtcataactgattgctcaaccaggatttcactcttcaaagccaaagaggctacactgctcctggctgtgt
cgaacctgtgctttgatcctatcctgtactatcacctctcaaaagcattccgctcaaggtcactgagacttttgcctc
```

| Sequences |
| --- |
| Probe Set ID | acctaaagagaccaaggctcagaaagaaaaattaagatgtgaaaataatgcataaaagacaggatttttttgtg
ctaccaattctggccttactgga 202988_s_at gtgaacagcttggcctttttttgggtgtcttgacaggccaagaagaacaaatgactcagaaccggattaacatgaa
agttatccaggcgcagagttgaagaagcataagcaagcaagacaaaaacagagagaccgcaaggagga
agatctgtggtactgtcataaaaaacagtggagctctgtattagaaaagcccctcagaactgggaaggccaggt
aactctagttacacagaaactggtactaaagtctatcaaactgattacacagactgtaagaattcaaagtcaact
gacatctatgctacatatattatatagtttgtacttgactatgagccattaacttaaagcatatgtttcaaatagccattg
ctactattccttgtccggtgtaattt-
tattttattgttttttactttggaagagatgaactgtgtatttaacttaagctattgctct
taaaaccaggg 213418_at ggttcatgaagccgagcagtacaaggctgaggatgaggcccagagggacagagtggctgccaaaaactcg
ctggaggcccatgtcttccatgtgaaaggttctttgcaagaggaaagctttagggacaagattcccgaagagga
caggcgcaaaatgcaagacaagtgtcgggaagtccttgcctggctggagcacaaccagctggcagagaag
gaggagtatgagcatcagaagagggagctggagcaaatctgtcgccccatcttctccaggctctatgggggc
ctggtgtccctgggggcagcagttgtngcnctcaagcccnccaggggaccccagcaccggccccatcattg
aggaggttgattgaatggccctcgtgataagtcagctgtgactgtcagggctatgctatgggccttctagactgtct
tctatgatcctgcccttcagagatga 209901_x_at ccagcatctgctgagctatgagccaaaccagggatttacagggaggaaaagctttcggactgctgaaggccca
gcaggaagagaggctggatgagatcaacaagcaattcctagacgatcccaaatatagcagtgatgaggatct
gccctccaaactggaaggcttcaaagagaaatacatggagtttgaccttaatggaaatggcgatattgatatcat
gtccctgaaacgaatgctggagaaacttggagtccccaagactcacctagagctaaagaaattaattggagag
gtgtccagtggctccggggagacgttcagctaccctgactttctcaggatgatgctgggcaagagatctgccatc
ctaaaaatgatcctgatgtatgaggaaaaagcgagagaaaaggaaaagccaacaggcccccagccaag
aaagctatctct 205488_at cagccacacgcgaaggtgaccttaaacttttacagctgacggaaaaagcaaaaattaacaaatatgtgactat
ccttcatctacctaaaaaggggatgatgtgaaaccaggaaccatgtgccaagttgcagggtggggaggact
cacaatagtgcatcttggtccgatactctgagagaagtcaatatcaccatcatagacagaaaagtctgcaatgat
cgaaatcactataattttaaccctgtgattggaatgaatatggtttgtgctggaagcctccgaggtggaagagactc
gtgcaatggagattctggaagcccttttgttgtgcgagggtgttttccgagggtcacttcctttggccttgaaaataa
atgcggagaccctcgtgggcctggtgtctatattcttctctcaaagaaacacctcaactgga 217022_s_at tcaagtgggaagagcgctgttcaaggaccacctgagcgtgacctctgtggctgctacagcgtgttccagtgtcct
gccgggctgtgccgagccatggaaccatggggagaccttcacttgcactgctgcccaccccgagttgaagacc
ccactaaccgccaacatcacaaaatccggaaacacattccggcccgaggtccacctgctgccgccgccgtcg
gaggagctggccctgaacgagctggtgacgctgacgtgcctggcacgtggcttcagcccaaggatgtgctggtt
cgctggctgcaggggtcacaggagctgccccgcgagaagtacctgacttgggcatcccggcaggagcccag
ccagggcaccaccaccttcgctgtgaccagcatactgcgcgtggcagccgaggactggaagaaggggggac
accttctcctgcatggtgggccacgaggccctgccgctggccttcacacagaagaccatcgaccgcttggcgg
gtaaacccacccatgtcaatgtgtctgttgtcatggcgga 207339_s_at gcaggggctaggctgggagacgacgaaggaacaggcgtttctgacgagcgggacgcagttctcggacgcc
gaggggctggcgctcccgcaggacggcctctattacctctactgtctcgtcggctaccgggcgcggggccccc
tggcggcgggaccccccagggccgctcggtcacgctgcgcagctctctgtaccgggcgggggcgcctacg
ggccgggcactcccgagctgctgctcgagggcgccgagacggtgactccagtgctggacccggccaggaga
caagggtacgggcctctctggtacacgagcgtggggttcggcggcctggtgcagctccggaggggcgagagg
gtgtacgtcaacatcagtcaccccgatatggtggacttcgcgagagggaagaccttctttggggccgtgatggtg
gggtgagggaatatgagtgcgtggtgcgagtgcgtgaatattgggggcccggac 206337_at gtgggagtggcctgaagagtcctctgaatgaaccttctggcctcccacagactcaaatgctcagaccagctcttc
cgaaaaccaggccttatctccaagaccagagatagtggggagacttcttggcttggtgaggaaaagcggacat
cagctggtcaaacaaactctctgaaccctccctccatcgtttttcactgtcctccaagccagcgggaatggca
gctgccacgccgccctaaaagcacactcatccctccacttgccgcgtcgccctcccaggctctcaacagggga
gagtgtggtgtttcctgcaggccaggccagctgcctccgcgtgatcaaagccacactctgggctccagagtggg
gatgacatgcactcagctcttggctccactgggatggaggagaggcaagggaaatgtcagggcggga
gggtgacagtggccgcccaaggccacgagcttgttctttgttctttgtcacagggactgaaaacctctcctcatgtt
ctgctttcgattcgttaagagagcaacattttacccacaca -continued

| Sequences |
|---|
| Probe Set ID |

208894_at cgatcaccaatgtacctccagaggtaactgtgctcacgaacagccctgtggaactgagagagcccaacgtcct
catctgtttcatagacaagttcacccca 39729_at acacaattaggctggctaacggatagtgagcttgtgccctgcctaggtngcctgtgctgggtgtccancctgtgc
cccanctgggtgccnnnnnnnnnnnnnnnnnnggccagacctgccctccaaactccacagtatgg
gaccctggagggntannnnnnnnnnnnnnnnatgcctccacctagaagntgaatagtgacgccctcccccaa
gcccacccagccgcacacaggcctagaggtaaccaataaagt 209500_x_at catggagctccgaattcttgcgtgtgtgtagatgaggggcggggacgggcgccaggcattgttcagacctggt
cggggcccactggaagcatccagaacagcaccaccatctagcggccgctcgagggaagcacccgccggtt
ggccgaagtccacgaagccgccctctgctagggaaaaccccctggttctccatgccacacctctctccaggtgcc
ctctgcctcttcacccacaagaagccttatcctacgtccttctctccatctatcggacccagtttccatcactatctc
cagagatgtagctattatgcgcccgtctacagggggtgcccgacgatgacggtgccttcgcagtcaaattactctt
cgggtcccaaggtttggctttcacgcgctccattgccccggcgtggcaggccattccaagcccttccgggctgga
actggtgtcggaggagcctcgggtgtatcgtacgccctggtgttggtgttgcctcactcctctgagctcttctttctgat
caagcc 214677_x_at tcataagtgacttctacccgggagccgtgacagtggcctggaaggcagatagcagcccgtcaaggcgggag
tggagaccaccacaccctccaaacaaagcaacaacaagtacgcggccagcagctatctgagcctgacgcct
gagcagtggaagtcccacagaagctacagctgccaggtcacgcatgaagggagcaccgtggagaagaca
gtggcccctacagaatgttcataggttctcaaccctcac 210314_x_at catggagctccgaattcttgcgtgtgtgtagatgaggggcggggacgggcgccaggcattgttcagacctggt
cggggcccactggaagcatccagaacagcaccaccatctagcggccgctcgagggaagcacccgccggtt
ggccgaagtccacgaagccgccctctgctagggaaaaccccctggttctccatgccacacctctctccaggtgcc
ctctgcctcttcacccacaagaagccttatcctacgtccttctctccatctatcggacccagtttccatcactatctc
cagagatgtagctattatgcgcccgtctacagggggtgcccgacgatgacggtgccttcgcagtcaatttactctt
cgggtcccaaggtttggctttcacgcgctccattgccccggcgtggcaggccattccaagcccttccgggctgga
actggtgtcggaggagcctcgggtgtatcgtacgccctggtgttggtgttgcctcactcctctgagctcttctttctgat
caagcc 209138_x_at tctctgggctccaggctgaggacgaggctgattattactgctgctcalatgcaggtagttacactgtggttttcggcg
gagggaccaaactgaccgtcctaggtcagcccaaggctgccccctcggtcactctgttcccgccctcctctgag
gagcttcaagccaacaaggccacactggtgtgtctcataagtgacttctacccgggacgcgtgacagtggcctg
gaaggcagatagcagcccgtcaaggcgggagtggagaccaccacaccctccaaacaaagcaacaaca
agtacgcggccagcagctatctgagcctgacgcctgagcagtggaagtcccacagaagctacagctgccag
gtcacgcatgaagggagcaccgtggagaagacagtggcccctacagaatgtt 207831_x_at tgaggactggctgatgcccattctggaccagatggtgatggagcagaacacagagggtgtaaagtggacgcct
tctaagatgatcgcccggctgggcaaggagatcaacaacccagagtccgtgtattactgggcccagaagaac
cacatccctgtgtttagtcccgacacttacagacggctcgctgggcgacatgatcttcttccattcctacaagaaccc
gggcctggtcctggacatcgttgagggtgcccgaccagacgaggctgtcctcctggggcaagatccggtggat
gcacagcccgtcaaggtctatgctgacgcctcccctggtcttcccctgcttgtggctgaaacctttgcccagaaga
tggatgccttcatgcatgagaagaacgaggactgagcggctgcggtcccaggaaggtcttaccccctcttctattt
attaatttgcagacccagcccctccctacttttggtcagctacgtctctagaa 215121_x_at aagccaacaaggccacactggtgtgtctcataagtgacttctacccgggagccgtgacagtggcctggaaggc
agatagcagcccgtcaaggcgggagtggagaccaccacaccctccaaacaaagcaacaacaagtacgc
ggccagcagctanctgagcctgacgcctgagcagtggaagtcccacanaagctacagctgccaggtcacgc
atgaagggagcaccgtggagaagacagtggcccctacagaatgttcataggttctnnanccctcanccccn
nccacgggagactagagctgcaggatcccaggggaggggtctctcctcccaccccaaggcatcaagcccttc
tccctgcactcnataaaccccnaataaatatnctcattngntcaancagaaannnnnnnnnannnnattttttttt
ctcacataaattgctagcctccccggggttctcagtgtgggtacagggaattctgcaccagtgtgaaaatcac
ccaagggagaggctcacagcctccctgagtcatctcaccagaggg 215946_x_at gcaacatgcaggttcctgctccagcgnggctcctggactggcnccngntgctgnccnggggtttcaatcca
agcataattcagtgaagcatgtgtttggcagnggacccagctcacgttttaggtcagcccaagncnaccccn
tcggtcantctgttcctgccgtcctntgaggagcnccaagccaacaaggccacactggtgtgtctcatgaatnac

| Sequences |
| --- |
| Probe Set ID | ttnnnncngggaatcttganggtgacctggaaggcagatggtacccncatcacccagngcgtggagangac
cacgccnctccaaacagagcaacancaagtacatggccagcagctacctgagcctgacgcccgagcagtg
gaggtcccgcagaagctacagctgccaggtcatgcatgaagggagcactgcagaagacggtggccctg
cagaatgttcataggttcccagccccaccccacccacaggggcctggagctgcaggatcccaggggaggc
gtc 204069_at aagccttacagttatcctgcaagggacaggaaggtctgatttgcaggattttttagagcattaaaataactatcagg
cagaagaatctttcttctcgcctaggatttcagccatgcgcgcgctctctctcttttctctctcttttcctctctctccctcttt
ctagcctggggcttgaatttgcatgtctaattcatttactcaccatatttgaattggcctgaacagatgtaaatcggga
aggatgggaaaaactgcagtcatcaacaatgattaatcagctgttgcaggcagtgtcttaaggagactggtagg
aggaggcatggaaaccaaaaggccgtgtgtttagaagcctaattgtcacatcaagcatcattgtccccatgcaa
caaccaccaccttatacatcacttcctgttttaagcagctctaaaacatagactgaagamattmaatatgttgactt
tatttctgagcaaagcatcggtcatgtgtgtatttttttcatagtcccaccttggagcatttatg 204698_at caagttcatccggcctgagggagagatcaccgattacagaacccgggtcagcggggtcacccctcagcacat
ggtgggggccacaccatttgccgtggccaggctagagatcctgcagctcctgaaaggcaagctggtggtgggt
catgacctgaagcacgacttccaggcactgaaagaggacatgagcggctacacaatctacgacacgtccact
gacaggctgttgtggcgtgaggccaagctggaccactgcaggcgtgtctccctgcgggtgctgagtgagcgcct
cctgcacaagagcatccagaacgcctgcttggacacagctcggtggaagatgcgagggcaacgatggagc
tctatcaaatctcccagagaatccgagcccgccgagggctgcccgcctggctgtgtcagactgaagcccatc
cagcccgttccgcagggactagaggctttcggcttttttgggaca 209906_at gaaagcaaggcagtccattcagggaattctggaggcagccttcagtgaggagctcacacgttccacccactgt
ccctcaaacaatgtcatttcagaaagaaatagtacaactgtgtgaaaatgtggagcagccaacaagcagggg
ctcttaggcaatcacatagtgaaagttataagaggatgaagtgatatggtgagcagcggacttcaaaaactgtc
aaagaatcaatccagcggttctcaaacggtacacagactattgacatcagcatcacctagaaacttgttagaaa
tgcaaattctcaagccgcatcccagacttgctgaatcggaatctctgggggttgggacccagcaagggcactta
acaaaccccgtttctgattaatgctaaatgtaagaatcattgtaaacattagttctatttctatcccaaactaagc 205608_s_at agagcagcctgatcttacacggtgctgatttcagcactaaagatgctgataatgacaactgtatgtgcaaatgtgc
cctcatgttaacaggaggatggtgtttgatgcttgtggcccctccaatctaaatggaatgttctatactgcgggac
aaaaccatggaaaactgaatgggataaagtggcactacttcaaagggcccagttactccttacgttccacaact
atgatgattcgacctttagattttttgaaagcgcaatgtcagaagcgattatgaaagcaacaaagaaatccggag
aagctgccaggtgagaaactgtttgaaaaacttcagaagcaaacaatattgtctcccttccagcaataagtggtag
ttatgtgaagtcaccaaggttcttgaccgtgaatctggaccgtttgagttcacaagagtctctacttggggtgaca
gtgctcacgtggctcgactatagaaaactccactgactgtcgggcttaaaaagggaagaaactgctgagcttg
ctgtgcttcaaactactact 205927_s_at tccacacacggccaggcctgtttatctacactgctgcccactcctctctctccagctccacatgctgtacctggatcatt
ctgaagcaaattccgagcattacatcattttgtccataaatattctaacatccttaaatatacaatcggaattcaag
catctcccattgtcccacaaatgtttggctgttttttgtagttggattgtttgtattaggattcaagcaaggcccatatattg
catttatttgaaatgtctgtaagtctcttttccatctacagagtttagcacatttgaacgttgctggttgaaatcccgagt
gtcatttgacatggttctctgaacttatctttcctataaaatggtagttagatctggaggtctgattttgtggcaaaaata
cttcctaggtggtgctgggtacttcttgttgcatcctgtcaggaggcagataatgctggtgcctctctattggtaatgtt
aagactgctgggtgggtttggagttcttggc 215051_x_at tgctgaaaaccctccagtcagcgcttatcccttctgctctctcccctcacccagagaaatacatggagtttgacctt
aatggaaatggcgatattgatatcatgtccctgaaacgaatgctggagaaacttggagtccccaagactcacct
agagctaaagaaattaattggagaggtgtccagtggctccggggagacgttcagctgacctttctcaggat
gatgctgggcaagagatctgccatcctaaaaatgatcctgatgtatgaggaaaaagcgagagaaaaggaaa
agccaacaggccccccagccaagaaagctatctctgagttgccctgatttgaagggaaaagggatgatggga
ttgaaggggcttctaatgacccagatatgg 205609_at gtttaccatcaagtctttttttatatt-
tatgtgtctgtattctaccccttttttgccttacaagtgatatttgcaggtattataccat
ttttctattcttggtggcttcttcatagcaggtaagcctctccttctaaaaacttctcaactgttttcatttaagggaaaga
aaatgagtattttgtcctttttgtgttcctacagacactttcttaaaccagttttttggataaagaatactatttccaaactca
tattacaaaaacaaaataaaataataaaaaaaagaaagcatgatatttactgttttgttgtctgggtttgagaaatga
aatattgtttccaattatttataataaatcagtataaaatgtttttatgattgttatgtgtattatgtaatacgtacatgtttatg
gcaatttaacatgtgtattcttttcatttaattgtttcagaataggataattaggtattcgaattttgtctttaaaattcatgtg
gtttctatgcaaagttcttcatatcatcaca

| Sequences |
| --- |
| Probe Set ID |

202890_at

```
aatgatggaatgttgactgtgtttggcacacaggacacggaccttcatggaagtccttgctctgcgtggcatctgtc
agcttttcacctttcattcttattcttcacttttgctgctgagcctagctgtacaaacttgcactttcatttgctaatataaatt
cagttttattttaccattttagagactactaatgattaaatgtagaaggagagggtgcacatgtttttatgtggagtgttt
aaaagataaatttataccactgtaatgtgcagctttttattaaaagagaaattggttgaactgctaggttgaatgaga
gacttcatctattggactattttttttaatccaggcatatggtctttagtaatggcttgtaatttgtgaaaacattaatttgg
gggttttccctgttttcagttgtccatgtacacatagtcattatattagaaaagaaagctgttcaacaaacttgtttaattt
gtttaaatcaacatagcatgaaacaccaaat
```

203485_at

```
aagcagtcgaccgcacttatggtaatcagttttgtataacttaaaataattaaataaatgaatAaatccaaaacaa
acatgcagtactttgttgtatgggattggtgggctgatttacatgtatggttactaaaaagtaccagcatgttaactt
attacaatttgtattactttctctgtagttcctaatggattcaattacggactctggatatttgcactt
```

The invention claimed is:

1. A method of determining the response to tipifarnib in a person with acute myeloid leukemia (AML) comprising: a) measuring the expression of RASGRP1 in a biological sample from the person, b) measuring the expression of APTX in a biological sample from the person, c) determining the ratio of the expression of RASGRP1 to that of APTX, and d) identifying the person as one who will respond to tipifarnib if the ratio is less than one.

2. The method of claim 1 in which the AML is selected from newly diagnosed, relapsed or refractory.

* * * * *